United States Patent
Zhang

(10) Patent No.: US 11,801,280 B2
(45) Date of Patent: Oct. 31, 2023

(54) DRUG FOR TREATING LEUKOPENIA, PREPARATION METHOD THEREOF AND USE THEREOF

(71) Applicant: HUBEI MONYAN PHARMACEUTICAL CO., LTD., Hubei (CN)

(72) Inventor: Min Zhang, Hubei (CN)

(73) Assignee: HUBEI MONYAN PHARMACEUTICAL CO., LTD., Hubei (CN)

( * ) Notice: Subject to any disclaimer, the term of this patent is extended or adjusted under 35 U.S.C. 154(b) by 230 days.

(21) Appl. No.: 17/415,969

(22) PCT Filed: Apr. 8, 2020

(86) PCT No.: PCT/CN2020/083630
§ 371 (c)(1),
(2) Date: Jun. 18, 2021

(87) PCT Pub. No.: WO2020/238420
PCT Pub. Date: Dec. 3, 2020

(65) Prior Publication Data
US 2021/0379138 A1 Dec. 9, 2021

(30) Foreign Application Priority Data
May 29, 2019 (CN) .......................... 201910454475.0

(51) Int. Cl.
| A61K 36/899 | (2006.01) |
| A61K 9/08 | (2006.01) |
| A61K 36/232 | (2006.01) |
| A61K 36/296 | (2006.01) |
| A61K 36/48 | (2006.01) |
| A61K 36/481 | (2006.01) |
| A61K 36/484 | (2006.01) |
| A61K 36/487 | (2006.01) |
| A61K 36/714 | (2006.01) |
| A61K 36/74 | (2006.01) |
| A61K 36/77 | (2006.01) |
| A61K 36/8968 | (2006.01) |
| A61K 9/00 | (2006.01) |

(52) U.S. Cl.
CPC .......... *A61K 36/899* (2013.01); *A61K 9/0053* (2013.01); *A61K 9/08* (2013.01); *A61K 36/232* (2013.01); *A61K 36/296* (2013.01); *A61K 36/48* (2013.01); *A61K 36/481* (2013.01); *A61K 36/484* (2013.01); *A61K 36/487* (2013.01); *A61K 36/714* (2013.01); *A61K 36/74* (2013.01); *A61K 36/77* (2013.01); *A61K 36/8968* (2013.01); *A61K 2236/331* (2013.01); *A61K 2236/333* (2013.01); *A61K 2236/37* (2013.01); *A61K 2236/51* (2013.01)

(58) Field of Classification Search
None
See application file for complete search history.

(56) References Cited

FOREIGN PATENT DOCUMENTS

| CN | 1657093 A | * | 8/2005 |
| CN | 1657093 A | | 8/2005 |
| CN | 101234181 A | | 8/2008 |
| CN | 101234181 B | | 4/2011 |
| CN | 104338031 A | | 2/2015 |
| CN | 104547660 A | | 4/2015 |
| CN | 104688722 B | | 10/2019 |

OTHER PUBLICATIONS

Zhang, H.-F., et al., Simultaneous extraction of epimedin A, B, C and icariin from Herba Epimedii by ultrasonic technique, Ultrasonics Sonochemistry 15 (2008) 376-385 (Year: 2008).*
International Search Report and Written Opinion from PCT/CN2020/083630 dated Jul. 6, 2020.
Extended European Search Report from European Patent Application No. 20814100.2 dated May 16, 2022.
Ma Lx et al.; "The prophylactic use of Chinese herbal medicine for chemotherapy-induced leukopenia in oncology patients: a systematic review and meta—analysis of randomized clinical trials"; Supportive Care in Cancer, Springer Berlin Heidelberg, Berlin/Heidelberg, vol. 23, No. 2, Oct. 23, 2014, pp. 561-579.

* cited by examiner

*Primary Examiner* — H. Sarah Park
(74) *Attorney, Agent, or Firm* — Dilworth & Barrese, LLP

(57) ABSTRACT

The present invention relates to a drug for treating leukopenia, its preparation method and use thereof. The drug of the invention is prepared from 200-30 parts by weight of Folium Epimedii, 100-160 parts by weight of Fructus Psoraleae, 60-120 parts by weight of Radix Aconiti Lateralis Preparata (Processed), 200-300 parts by weight of Fructus Lycii, 200-300 parts by weight of Radix Astragali, 200-300 parts by weight of Caulis Spatholobi, 200-300 parts by weight of Radix Rubiae, 100-160 parts by weight of Radix Angelicae Sinensis, 200-300 parts by weight of Rhizoma Phragmitis, 100-160 parts by weight of Radix Ophiopogonis and 100-160 parts by weight of Radix et Rhizoma Glycyrrhizae. The drug of the invention comprises chemical substances with weight ratios as follows: Leucine:guanosine:psoralenoside:isopsoralenoside:calycosin-7-glucoside:liquiritin:icariin A:1,3-dihydroxyl-2-hydroxymethylanthraquinone:epimedin A:epimedin B:epimedin C:icariin:1,3,6-trihydroxy-2-methylanthraquinone:glycyrrhizic acid= (0.13-0.27):(0.04-0.11):(0.11-0.34):(0.09-0.34):(0.05-0.11): (0.16-0.26):(0.09-0.12):(0.17-0.35):(0.11-0.16):(0.17-0.26): (0.49-0.59):1.00:(0.16-0.24):(0.08-0.14).

13 Claims, 2 Drawing Sheets

DRUG FOR TREATING LEUKOPENIA, PREPARATION METHOD THEREOF AND USE THEREOF

TECHNICAL FIELD

The present invention relates to the pharmaceutical field, specifically, the present invention relates to a drug for treating leukopenia, its preparation method and use thereof.

BACKGROUND ARTS

Shengbai Oral Solution, a traditional Chinese medicine preparation, is prepared from Folium Epimedii, Fructus Psoraleae, Radix Aconiti Lateralis Preparata (Processed), Fructus Lycii, Radix Astragali, Caulis Spatholobi, Radix Rubiae, Radix Angelicae Sinensis, Rhizoma Phragmitis, Radix Ophiopogonis, Radix et Rhizoma Glycyrrhizae. It has the function of reinforcing the kidney and invigorating the spleen function, replenish qi and blood (vital energy), that can be used for leukopenia induced by radiotherapy or chemotherapy for cancer patients with symptoms of spleen-kidney yang deficiency and qi-blood (vital energy) deficiency, such as lassitude, lack of strength, shortness of breath, spiritlessness, fear of cold and cold limbs, reduced food intake, sloppy stool, soreness and weakness in the lower back and knees. Clinically, it is mainly used to prevent and treat leukopenia and promote the growth of leucocytes in the process of radiotherapy and chemotherapy for malignancies. CN200410078100.2 disclosed a traditional Chinese medicine effervescent granule which was mainly used for the treatment of leukopenia caused by radiotherapy or chemotherapy for cancer patients with symptoms of spleen-kidney yang deficiency and qi-blood (vital energy) deficiency. The effervescent granule was prepared from 11 kinds of traditional Chinese medicines including Folium Epimedii, and 10-50 parts by weight of β-cyclodextrin (a cosolvent). Spray drying and dry granulation was adopted in the preparation process, using β-cyclodextrin as the cosolvent, so that the active ingredients could be retained as completely as possible, facilitating the continuous large-scale production under GMP conditions. CN200810007189.1 disclosed a drug used for the prevention and treatment of leukopenia during cancer radiotherapy and chemotherapy, and its formulation and weight ratios were described as 6-8 parts of Folium Epimedii, 3-6 parts of Fructus Psoraleae, 1-3 parts of Radix Aconiti Lateralis Preparata (Processed), 1-3 parts of Fructus Lycii, 6-8 parts of Radix Astragali, 6-8 parts of Caulis Spatholobi, 6-8 parts of Radix Rubiae, 3-6 parts of Radix Angelicae Sinensis, 6-8 parts of Rhizoma Phragmitis, 3-6 parts of Radix Ophiopogonis, 3-6 parts of Radix et Rhizoma Glycyrrhizae, the preferred dosage form was an oral solution. CN201410701679.7 disclosed a processing method of Shengbai mixture with high content of icariin, that Fructus Psoraleae, Radix Aconiti Lateralis Preparata (Processed), Fructus Lycii, Radix Astragali, Caulis Spatholobi, Radix Rubiae, Radix Angelicae Sinensis, Rhizoma Phragmitis, Radix Ophiopogonis, Radix et Rhizoma Glycyrrhizae were added into the extraction tank, soaked with water, heated to boil, then Folium Epimedii was added, kept boiling for 0.5-1.5 hours, and then filtering, concentrating, alcohol precipitation, and alcohol recovering were carried out to get the product. Advantages: In the above processing, Fructus Psoraleae, Radix Aconiti Lateralis Preparata (Processed), Fructus Lycii, Radix Astragali, Caulis Spatholobi, Radix Rubiae, Radix Angelicae Sinensis, Rhizoma Phragmitis, Radix Ophiopogonis, Radix et Rhizoma Glycyrrhizae were added into the extraction tank first, soaked with water, heated to boiling, then Folium Epimedii was added, the content of icariin in the Shengbai mixture finished product could reach as high as 19 mg/10 ml. But the efficacy of Shengbai products in above mentioned patents is not stable, and the group of active ingredients bringing forth the efficacy is not known.

SUMMARY OF THE INVENTION

In order to solve the above technical problems, the present invention aims to provide a drug for treating leukopenia with definite efficacy.

The present invention is also intended to provide a method for preparing the drug.

To achieve above objectives, the present invention provides the following technical solutions:

Preferably, a drug for treating leukopenia is prepared from 200-300 parts by weight of Folium Epimedii, 100-160 parts by weight of Fructus Psoraleae, 60-120 parts by weight of Radix Aconiti Lateralis Preparata (Processed), 200-300 parts by weight of Fructus Lycii, 200-300 parts by weight of Radix Astragali, 200-300 parts by weight of Caulis Spatholobi, 200-300 parts by weight of Radix Rubiae, 100-160 parts by weight of Radix Angelicae Sinensis, 200-300 parts by weight of Rhizoma Phragmitis, 100-160 parts by weight of Radix Ophiopogonis, 100-160 parts by weight of Radix et Rhizoma Glycyrrhizae. The drug of the present invention comprises chemical substances with weight ratios as shown in Table 1.

TABLE 1

| Peak number | Chemical substance | Weight ratio relative to icariin |
|---|---|---|
| 1 | Leucine | 0.13-0.27 |
| 2 | Guanosine | 0.04-0.11 |
| 3 | Psoralenoside | 0.11-0.34 |
| 4 | Isopsoralenoside | 0.09-0.34 |
| 5 | Calycosin-7-glucoside | 0.05-0.11 |
| 6 | Liquiritin | 0.16-0.26 |
| 7 | Icariin A | 0.09-0.12 |
| 8 | 1,3-dihydroxyl-2-hydroxymethylanthraquinone | 0.17-0.35 |
| 9 | Epimedin A | 0.11-0.16 |
| 10 | Epimedin B | 0.17-0.26 |
| 11 | Epimedin C | 0.49-0.59 |
| 12 | Icariin | 1.00 |
| 13 | 1,3,6-trihydroxy-2-methylanthraquinone | 0.16-0.24 |
| 14 | Glycyrrhizic acid | 0.08-0.14 |

More preferably, a drug for treating leukopenia of the invention is prepared from 240 parts by weight of Folium Epimedii, 120 parts by weight of Fructus Psoraleae, 80 parts by weight of Radix Aconiti Lateralis Preparata (Processed), 240 parts by weight of Fructus Lycii, 240 parts by weight of Radix Astragali, 240 parts by weight of Caulis Spatholobi, 240 parts by weight of Radix Rubiae, 120 parts by weight of Radix Angelicae Sinensis, 240 parts by weight of Rhizoma Phragmitis, 120 parts by weight of Radix Ophiopogonis, 120 parts by weight of Radix et Rhizoma Glycyrrhizae.

More preferably, the drug of the present invention comprises chemical substances with weight ratios as shown in Table 2.

TABLE 2

| Peak number | Chemical substance | Weight ratio relative to icariin |
|---|---|---|
| 1 | Leucine | 0.13-0.22 |
| 2 | Guanosine | 0.06-0.10 |
| 3 | Psoralenoside | 0.14-0.26 |
| 4 | Isopsoralenoside | 0.12-0.23 |
| 5 | Calycosin-7-glucoside | 0.07-0.11 |
| 6 | Liquiritin | 0.19-0.25 |
| 7 | Icariin A | 0.10-0.12 |
| 8 | 1,3-dihydroxyl-2-hydroxymethylanthraquinone | 0.18-0.28 |
| 9 | Epimedin A | 0.11-0.14 |
| 10 | Epimedin B | 0.21-0.25 |
| 11 | Epimedin C | 0.50-0.54 |
| 12 | Icariin | 1.00 |
| 13 | 1,3,6-trihydroxy-2-methylanthraquinone | 0.19-0.23 |
| 14 | Glycyrrhizic acid | 0.09-0.11 |

More preferably, the drug of the present invention comprises chemical substances with weight ratios as shown in Table 3.

TABLE 3

| Peak number | Chemical substance | Weight ratio relative to icariin |
|---|---|---|
| 1 | Leucine | 0.14-0.20 |
| 2 | Guanosine | 0.06-0.09 |
| 3 | Psoralenoside | 0.19-0.24 |
| 4 | Isopsoralenoside | 0.17-0.23 |
| 5 | Calycosin-7-glucoside | 0.09-0.10 |
| 6 | Liquiritin | 0.23-0.25 |
| 7 | Icariin A | 0.10-0.12 |
| 8 | 1,3-dihydroxyl-2-hydroxymethylanthraquinone | 0.20-0.23 |
| 9 | Epimedin A | 0.12-0.13 |
| 10 | Epimedin B | 0.22-0.24 |
| 11 | Epimedin C | 0.51-0.52 |
| 12 | Icariin | 1.00 |
| 13 | 1,3,6-trihydroxy-2-methylanthraquinone | 0.20-0.23 |
| 14 | Glycyrrhizic acid | 0.09-0.11 |

Relative retention time (RRT) of the said chemical substances within the drug of the invention by ultra performance liquid chromatography (UPLC) is shown in Table 4.

TABLE 4

| Peak number | Chemical substance | RRT |
|---|---|---|
| 1 | Leucine | 0.120-0.124 |
| 2 | Guanosine | 0.163-0.167 |
| 3 | Psoralenoside | 0.576-0.582 |
| 4 | Isopsoralenoside | 0.593-0.599 |
| 5 | Calycosin-7-glucoside | 0.638-0.644 |
| 6 | Liquiritin | 0.661-0.667 |
| 7 | Icariin A | 0.788-0.792 |
| 8 | 1,3-dihydroxyl-2-hydroxymethylanthraquinone | 0.887-0.894 |
| 9 | Epimedin A | 0.944-0.952 |
| 10 | Epimedin B | 0.964-0.968 |
| 11 | Epimedin C | 0.980-0.981 |
| 12 | Icariin | 1.000 |
| 13 | 1,3,6-trihydroxy-2-methylanthraquinone | 1.055-1.058 |
| 14 | Glycyrrhizic acid | 1.138-1.144 |

More preferably, the drug of the invention comprises the following chemical substances: Glutamic acid, proline, 5-hydroxymethylfurfural, nicotinic acid, leucine, adenosine, guanosine, senkyunolide A, songorine, fuziline, p-hydroxy benzaldehyde, psoralenoside, isopsoralenoside, vanillin, p-hydroxy-cinnamic acid, calycosin-7-glucoside, liquiritin, ferulic acid, catechin, benzoylmesaconine, icariin A, ononin, 1,3-dihydroxyl-2-hydroxymethylanthraquinone, epimedin A, epimedin B, epimedin C, icariin, 1,3,6-trihydroxy-2-methylanthraquinone, psoralen, isopsoralen, glycyrrhizic acid, ligustilide, icarisid I, baohuoside I, neobavaisoflavone, bavachin, bavachinin, isobavachalcone.

The drug of the invention can be prepared by a process comprising steps of:

Step (1): Taking 200-30 parts by weight of Folium Epimedii, 100-160 parts by weight of Fructus Psoraleae, 60-120 parts by weight of Radix Aconiti Lateralis Preparata (Processed), 200-300 parts by weight of Fructus Lycii, 200-300 parts by weight of Radix Astragali, 200-300 parts by weight of Caulis Spatholobi, 200-300 parts by weight of Radix Rubiae, 100-160 parts by weight of Radix Angelicae Sinensis, 200-300 parts by weight of Rhizoma Phragmitis, 100-

160 parts by weight of Radix Ophiopogonis and 100-160 parts by weight of Radix et Rhizoma Glycyrrhizae, standby;

Step (2): Adding water into the above formulated amount of prepared slices of Chinese crude drugs (except Folium Epimedii) and heating to boiling, then adding formulated amount of Folium Epimedii, continuing heating to boiling, carrying out timing extraction, then filtering to get the filtrate for the first time, adding water to the residues for a second-time extraction, filtering to get the filtrate for the second time, combining the two-time filtrates, concentrating to get the extract I;

Step (3): Conducting alcohol precipitation on the extract I, then standing, filtering, recovering alcohol to get the Shengbai extract.

Preferably, in step (3) of the invention, slowly adding 85-95% ethanol into extract I of the invention at the ratio of extract I:ethanol=1:1-2 (mg/ml), adding while stirring, so that extract I can be evenly dispersed, and then adding 85-95% ethanol to alcohol content of 60-80%, adding while stirring, standing, recovering ethanol, to obtain the Shengbai extract.

In the above step (2), the content of icariin can be enhanced by changing the sequence of adding Folium Epimedii.

In the above step (3), the overall content of chemical substances within the drug of the invention can be improved by adjusting the ratio of ethanol to water and the addition method during alcohol precipitation.

Preferably, the drug of the invention can be prepared by a process comprising steps of:

Step (1): Taking 200-30 parts by weight of Folium Epimedii, 100-160 parts by weight of Fructus Psoraleae, 60-120 parts by weight of Radix Aconiti Lateralis Preparata (Processed), 200-300 parts by weight of Fructus Lycii, 200-300 parts by weight of Radix Astragali, 200-300 parts by weight of Caulis Spatholobi, 200-300 parts by weight of Radix Rubiae, 100-160 parts by weight of Radix Angelicae Sinensis, 200-300 parts by weight of Rhizoma Phragmitis, 100-160 parts by weight of Radix Ophiopogonis and 100-160 parts by weight of Radix et Rhizoma Glycyrrhizae, standby;

Step (2): Adding water into the above formulated amount of prepared slices of Chinese crude drugs (except Folium Epimedii) and heating at 75-100° C. to boiling, then adding formulated amount of Folium Epimedii, continuing heating at 75-100° C. to boiling, conducting 0.5-1.5 h of extraction, then filtering to get the filtrate for the first time, adding water to the residues for a second-time extraction, filtering to get the filtrate for the second time, combining the two-time filtrates, concentrating to relative density of 1.24-1.27 (25±5° C.) to get the extract I;

Step (3): Slowly adding 90% ethanol into extract I of the invention at the ratio of extract 1:ethanol=1:1-1.2, adding while stirring, so that extract I can be evenly dispersed, and then adding 90% ethanol to alcohol content of 70%, adding while stirring, standing for 72 h for alcohol precipitation, filtering, recovering ethanol, concentrating to obtain the Shengbai extract.

The chemical substances of glutamic acid, guanosine, psoralenoside, isopsoralenoside, calycosin-7-glucoside, liquiritin, icariin A, 1,3-dihydroxyl-2-hydroxymethylanthraquinone, epimedin A, epimedin B, epimedin C, icariin, 1,3,6-trihydroxy-2-methylanthraquinone, glycyrrhizic acid within the drug of the invention were analyzed and identified through HPLC-ESI-MS.

In one embodiment example of the invention, the invention provides a pharmaceutical preparation of the drug of the invention, wherein said pharmaceutical preparation comprises the drug of the invention and one or more pharmaceutically acceptable carriers. The weight percentage of the drug of the invention in the pharmaceutical preparation can be 0.1%-99.9%, and the rest are pharmaceutically acceptable carriers.

The pharmaceutical preparation of the invention is in the form of unit dose pharmaceutical preparation. The unit dose refers to the unit of preparation, such as per tablet, per capsule, per bottle of oral solution, per bag of granules, etc. It can be prepared by any method well known in pharmaceutical field, including the steps for combining the traditional Chinese medicine composition of the present invention with a carrier or carriers constituting one or more auxiliary components. In general, the preparation process is as follows: Combining well the traditional Chinese medicine composition of the present invention with liquid carrier/carriers or finely pulverized solid carrier/carriers or the combination of both uniformly, then, if necessary, the obtained product can be made into the required preparation. The pharmaceutical preparation of the present invention can be prepared from the traditional Chinese medicine composition of the invention and pharmaceutical carrier/carriers by using standard pharmaceutical techniques, including mixing, granulation and tabletting. It is well known to technicians in the field that the form and characteristics of a pharmaceutically acceptable carrier or diluent depend on the amount of the active ingredient mixed with, administration route and other known factors.

The pharmaceutical preparation of the invention can be in any one of the pharmaceutical dosage forms including: Tablets, sugar coated tablets, film coated tablets, enteric coated tablets, capsules, hard capsules, soft capsules, oral solutions, buccal preparations, granules, electuary, pills, powders, pastes, sublimed preparations, suspensions, dust powders, solutions, injections, suppositories, ointments, plasters, creams, sprays, drops, patches.

Preferably, the pharmaceutical preparation of the invention can be an oral preparation, selected from any one of capsules, tablets, oral solutions, granules, pills, powders, sublimed preparations, pastes, and so on.

The oral preparation can contain commonly used excipients, such as binders, fillers, diluents, tabletting aids, lubricants, disintegrants, colorants, flavoring agents and wetting agents, and the tablets can be coated if necessary.

Applicable fillers include cellulose, mannitol, lactose and other similar fillers. Suitable disintegrants include starch, polyvinylpyrrolidone and starch derivatives, such as sodium starch glycolate. Suitable lubricants include, for example, magnesium stearate. Suitable pharmaceutically acceptable wetting agents include sodium lauryl sulfate.

The oral solid compositions can be prepared from common methods such as mixing, filling and tabletting. Repeated mixing allows the active ingredients to be distributed throughout those compositions using large amounts of fillers.

The oral liquid preparation can be selected from aqueous or oily suspensions, solutions, emulsions, syrups or elixirs, or a dry product that can be reconstituted by water or other suitable carrier before use. The liquid preparation may contain conventional additives, such as suspension agents including sorbitol, syrup, methyl cellulose, gelatin, hydroxyethyl cellulose, carboxymethyl cellulose, aluminum stearate gel or hydrogenated edible fats; emulsifiers including lecithin, dehydrated sorbitol monoleate or Arabic gum; non-water-based carriers (which may include edible oils) including almond oil, fractionated coconut oil, oily esters like glyceryl esters, propylene glycol or ethanol; preservatives including methyl p-hydroxybenzoate or propyl p-hydroxybenzoate or sorbic acid, and may contain conventional flavouring agents or colorants, if necessary.

For injections, the liquid unit dosage form prepared contains the active substance(s) of the invention and sterile carrier(s). Depending on the carrier and concentration thereof, the compound can be suspended or dissolved. The solution is usually prepared by dissolving the active substance(s) in a carrier, filtering and sterilizing before loading into a suitable vial or ampoule, and then sealing. Excipients, such as a local anesthetic, preservative(s) and buffer(s) can also be dissolved in the carrier. To improve its stability, the composition can be frozen in a vial, with water removed under vacuum.

When preparing a drug product, suitable pharmaceutically acceptable carriers can be selectively added, and the said pharmaceutically acceptable carriers can be selected from one or more in the group consists of: Mannitol, sorbitol, sodium metabisulfite, sodium bisulfite, sodium thiosulfate, cysteine hydrochloride, thioglycolic acid, methionine, vitamin C, EDTA disodium, EDTA calcium sodium, monovalent alkali metal carbonate, acetate, phosphate or its aqueous solution, hydrochloric acid, acetic acid, sulfuric acid, phosphoric acid, amino acids, sodium chloride, potassium chloride, sodium lactate, xylitol, maltose, glucose, fructose, dextran, glycine, starch, sucrose, lactose, mannite, silicic derivatives, cellulose and its derivatives, alginates, gelatin, polyvinyl pyrrolidone, glycerin, Tween 80, agar-agar, calcium carbonate, calcium bicarbonate, surfactants, polyethylene glycol, cyclodextrin, β-cyclodextrin, phospholipid material, kaolin, talc, and calcium stearate or magnesium stearate, and so on.

Preferably, the pharmaceutical preparation of the invention can be an oral solution or granule.

In another embodiment example, the present invention provides an oral solution for promoting leucocytes, comprising the drug of the invention and flavoring agents. The weight ratio of flavoring agents to drug is 0.1-1%.

Wherein said flavoring agents include (but not limited) steviosin, sucrose, white granulated sugar, and so on. Preferably, the said flavoring agent is steviosin.

The preparation method for preparing the Shengbai oral solution of the invention comprises steps of: Adding purified water and steviosin to the drug of the invention, stirring, adjusting pH value to 5.0-6.0, heating to boiling for 30-50 min, refrigerating, taking the supernatant, adjusting pH value to 6.5-7.5, adjusting the volume to required level, filtering, filling, sterilizing.

Preferably, adding purified water and steviosin to the drug, stirring, adjusting pH value to 5.0-5.5, heating to boiling for 30 min, refrigerating for 48 h, taking the supernatant, adjusting pH value to 7.0-7.3, adjusting the volume to required level, filtering, filling, then sterilizing.

The said pH regulator is selected from sodium hydroxide solution or sodium bicarbonate solution.

The steps of preparing the oral solution of the invention can not only improve the content of icariin and the overall pharmaceutical chemical substances in the finished product, but also adjust the taste and improve the clarity by adjusting the pH twice.

Compared with the prior art, the beneficial effects of the present invention are illustrated by the following experimental examples:

Example 1 Effect of Shengbai Oral Solution on the Prevention and Treatment of Cyclophosphamide Induced Leukopenia in Mice (1) Experimental Materials:

Shengbai oral solution 1: With the same formulation as embodiment 1 of the invention, processing in accordance with CN2014107016797, 20 ml/vial.

Shengbai oral solution 2: As embodiment 1 of the invention, 20 ml/vial.

Cyclophosphamide for injection was purchased from Jiangsu Hengrui Pharmaceutical Co., Ltd.

Experimental animals: Kunming mice, male, 6-8 weeks, weight 18-20 g.

(2) Experimental Method:

Modeling of leukopenia in mice: Mice were intraperitoneally injected with cyclophosphamide for 3 consecutive days, once a day, 100 mg/kg each time.

48 Kunming mice were randomly divided into 4 groups with 12 mice in each group, which were blank control group, model group, Shengbai oral solution 1 group and Shengbai oral solution 2 group. Blank control group: Saline was given intraperitoneally on day 1-3, and saline was given intragastrically for 14 consecutive days; Model group: Cyclophosphamide (100 mg/kg) was given intraperitoneally on day 1-3, and saline was given intragastrically for 14 consecutive days; Shengbai oral solution 1 group: Cyclophosphamide (100 mg/kg) was given intraperitoneally on day 1-3, and Shengbai oral solution 1 was given intragastrically for 14 consecutive days, once a day, 1 ml each time; Shengbai oral solution 2 group: Cyclophosphamide (100 mg/kg) was given intraperitoneally on day 1-3, and Shengbai oral solution 2 was given intragastrically for 14 consecutive days, once a day, 1 ml each time.

Blood sampling: Orbital blood was collected on day 4, day 9 and day 14, respectively.

(3) Experimental Results:

1) Effect of Shengbai Oral Solution on Cyclophosphamide Induced Leukopenia in Mice

TABLE 5

Effect of Shengbai Oral Solution on Cyclophosphamide Induced Leukopenia in Mice($\times 10^9$/L)

| Group | Day 4($\times 10^9$/L) | Day 9($\times 10^9$/L) | Day 14($\times 10^9$/L) |
|---|---|---|---|
| Blank control group | 9.86 ± 0.54** | 10.23 ± 0.48** | 10.08 ± 1.06** |
| Model group | 3.36 ± 1.33 | 3.71 ± 1.26** | 4.75 ± 1.42 |
| Shengbai oral solution 1 group | 5.26 ± 2.06* | 6.6 ± 1.64** | 8.03 ± 1.85** |

TABLE 5-continued

Effect of Shengbai Oral Solution on Cyclophosphamide Induced Leukopenia in Mice($\times 10^9$/L)

| Group | Day 4($\times 10^9$/L) | Day 9($\times 10^9$/L) | Day 14($\times 10^9$/L) |
|---|---|---|---|
| Shengbai oral solution 2 group | 5.57 ± 1.54* | 7.73 ± 1.07**# | 9.25 ± 1.48**# |

Note:
Compared with the model group, *<0.05, **<0.01;
Shengbai oral solution 2 group compared with Shengbai oral solution 1 group, #<0.05;

As shown in Table 5, the leukocytes in the peripheral blood of the mice in the model group decreased after giving cyclophosphamide, and showed significant difference compared with the blank control group (P<0.01). However, the leukopenia of mice treated with Shengbai oral solution was significantly relieved. On day 14, the leucocyte level in peripheral blood of mice in Shengbai oral solution 1 group and Shengbai oral solution 2 group basically returned to normal. Compared with Shengbai oral solution 1 group, Shengbai oral solution 2 group demonstrated significantly better effect (P<0.05), indicating that the drug of the invention can significantly improve the therapeutic effect.

Example 2: Effect of Shengbai Oral Solution on the Prevention and Treatment of Irradiation Induced Leukopenia in Mice (1) Experimental Materials:
Shengbai oral solution 1 and Shengbai oral solution 2 were supplied by Hubei Monyan Pharmaceutical Co., Ltd.;
Shengbai oral solution 1: With the same formulation as embodiment 1 of the invention, processing in accordance with CN2014107016797, 20 ml/vial.
Shengbai oral solution 2: As embodiment 1 of the invention, 20 ml/vial.
Experimental animals: Kunming mice, male, 6-8 weeks, weight 18-20 g.
(2) Experimental Method:
Modeling of leukopenia in mice: Except for the blank control group, mice in the other 3 groups underwent $^{60}$Co γ one-time whole-body uniform irradiation, the irradiation dose rate was $3.89\times 10^{-2}$ Gy·Kg$^{-1}$, the distance was 0.8 cm, the exposure dose was 6 Gy.
48 Kunming mice were randomly divided into 4 groups with 12 mice in each group, which were blank control group, model group, Shengbai oral solution 1 group and Shengbai oral solution 2 group Blank control group: Saline was given intragastrically for 14 consecutive days; Model group: Saline was given intragastrically for 14 consecutive days after the irradiation; Shengbai oral solution 1 group: Shengbai oral solution 1 was given intragastrically for 14 consecutive days after the irradiation, once a day, 1 ml each time; Shengbai oral solution 2 group: Shengbai oral solution 2 was given intragastrically for 14 consecutive days after the irradiation, once a day, 1 ml each time.
Blood sampling: Orbital blood was collected on day 1, day 3, day 7 and day 14, respectively.
(3) Experimental Results:
1) Effect of Shengbai Oral Solution on Irradiation Induced Leukopenia in Mice

TABLE 6

Effect of Shengbai Oral Solution on Irradiation Induced Leukopenia in Mice($\times 10^9$/L)

| Group | Day 1 ($\times 10^9$/L) | Day 3 ($\times 10^9$/L) | Day 7 ($\times 10^9$/L) | Day 14 ($\times 10^9$/L) |
|---|---|---|---|---|
| Blank control group | 10.33 ± 0.61** | 10.04 ± 0.27** | 10.68 ± 0.33** | 9.84 ± 0.84** |
| Model group | 3.43 ± 0.28 | 3.71 ± 0.45 | 4.01 ± 0.58** | 5.27 ± 0.73 |
| Shengbai oral solution 1 group | 3.37 ± 0.22 | 4.88 ± 0.88 | 6.64 ± 0.72** | 7.88 ± 1.07** |
| Shengbai oral solution 2 group | 3.28 ± 0.62 | 5.03 ± 1.27* | 7.83 ± 0.93**# | 9.39 ± 1.2**# |

Note: Compared with the model group, *<0.05, **<0.01;
Shengbai oral solution 2 group compared with Shengbai oral solution 1 group, #<0.05;

As shown in Table 6, the leukocytes in the peripheral blood of the mice in the model group decreased after the irradiation, and showed significant difference compared with the blank control group (P<0.01). However, the leukopenia of mice treated with Shengbai oral solution was significantly relieved. On day 14, the leucocyte level in peripheral blood of mice in Shengbai oral solution 1 group and Shengbai oral solution 2 group basically returned to normal. Compared with Shengbai oral solution 1 group, Shengbai oral solution 2 group demonstrated significantly better effect (P<0.05), indicating that the drug of the invention can significantly improve the therapeutic effect.

Example 3 Process Study

1. Influence of Different Ways of Adding Folium Epimedii on Icariin Content in Shengbai Extract.
1.1 Experimental Schemes
1.1.1 Experimental scheme (1): Based on the production process, adding the formulated amount of drinking water into the formulated amount of 11 kinds of prepared slices of Chinese crude drugs (including Folium Epimedii) and heating at 75-80° C. to boiling, carrying out timing extraction, then filtering to get the filtrate once, adding formulated amount of drinking water to the residues for a second-time extraction, filtering to get the filtrate once again, combining the two-time filtrates, concentrating to get the Shengbai extract (i.e. lot number 140301), then detecting the content of icariin thereof.

1.1.2 Experimental scheme (2): Based on the production process, adding the formulated amount of drinking water into the formulated amount of 10 kinds of prepared slices of Chinese crude drugs (not including Folium Epimedii) and heating at 75-80° C. to boiling, then adding formulated amount of Folium Epimedii, continuing heating at 75-80° C. to boiling, carrying out timing extraction, then filtering to get the filtrate once, adding formulated amount of drinking water to the residues for a second-time extraction, filtering to get the filtrate once again, combining the two-time filtrates, concentrating to get the Shengbai extract, then detecting the content of icariin thereof.

Note: Except for the change of adding sequence of Folium Epimedii, the other technical parameters remained unchanged.

1.2 Experimental Results and Analysis 1.2.1 Experimental Results

TABLE 7

|  | Scheme | Weight (g) | Concentration of icariin (mg/g) | Content of icariin (mg) | Transfer rate of icariin | Average transfer rate of icariin |
|---|---|---|---|---|---|---|
| Folium Epimedii | — | 120.0 | 7.20 | 864 | — | — |
| Detection 1-1 | (1) | 566.4 | 1.28 | 725 | 83.9% | 83.8% |
| Detection 1-2 | (1) | 545.5 | 1.32 | 720 | 83.3% | |
| Detection 1-3 | (1) | 563.6 | 1.29 | 727 | 84.1% | |
| Detection 2-1 | (2) | 559.2 | 1.46 | 816 | 94.5% | 94.8% |
| Detection 2-2 | (2) | 565.7 | 1.45 | 820 | 94.9% | |
| Detection 2-3 | (2) | 551.0 | 1.49 | 821 | 95.0% | |

1.2.2 Analysis of Experimental Results

Data of detection 1-1, 1-2 and 1-3 belong to scheme 1, data of detection 2-1, 2-2 and 2-3 belong to scheme 2, the average transfer rate of icariin in scheme 2 was about 10% higher than that in scheme 1. It indicates that, in the process of Shengbai mixture (oral solution) production, adding the said 10 kinds of prepared slices of Chinese crude drugs of the invention (not including Folium Epimedii) first and boiling with water, then adding Folium Epimedii for extraction can increase the content of icariin in Shengbai extract, about 10% higher than that in Scheme 1.

2. Influence of Different Ways of Adding Alcohol on Icariin Content in Shengbai Extract During Alcohol Precipitation in the Process of Shengbai Mixture (Oral Solution) Production.

2.1 Experimental Schemes 2.1.1 Experimental scheme (1): Based on the production process, taking 200 g of the concentrated extract of lot 140301 (extract density 1.24-1.27), adding 90% ethanol to alcohol content of 70%, adding while stirring, standing for 72 h for alcohol precipitation, recovering ethanol, to obtain the Shengbai extract, then detecting the content of icariin thereof.

2.1.2 Experimental scheme (2): Based on the production process, taking 200 g of the concentrated extract of lot 140301, slowly adding about 200 ml of 90% ethanol into the extract at the ratio of extract:ethanol=1:1-1.2, adding while stirring, so that the extract could be evenly dispersed, and then adding 90% ethanol to alcohol content of 70%, adding while stirring, standing for 72 h for alcohol precipitation, recovering ethanol, to obtain the Shengbai extract, then detecting the content of icariin thereof.

Note: Except for the change of ways of adding ethanol for alcohol precipitation, the other technical parameters remained unchanged.

2.2 Experimental Results and Analysis 2.2.1 Experimental Results

TABLE 8

|  | Scheme | Weight (g) | Concentration of icariin (mg/g) | Content of icariin (mg) | Transfer rate of icariin | Average transfer rate of icariin |
|---|---|---|---|---|---|---|
| Extract before alcohol precipitation | — | 200 | 1.30 | 260 | — | — |
| Detection 1-1 | (1) | 87.4 | 2.0 | 176 | 67.7% | 67.0% |
| Detection 1-2 | (1) | 88.6 | 1.95 | 173 | 66.5% | |
| Detection 1-3 | (1) | 92.3 | 1.89 | 174 | 66.9% | |
| Detection 2-1 | (2) | 95.1 | 2.32 | 221 | 84.9% | 85.2% |
| Detection 2-2 | (2) | 93.6 | 2.34 | 219 | 84.2% | |
| Detection 2-3 | (2) | 92.7 | 2.43 | 225 | 86.5% | |

2.2.2 Analysis of Experimental Results

Data of detection 1-1, 1-2 and 1-3 belong to scheme 1, data of detection 2-1, 2-2 and 2-3 belong to scheme 2, the average transfer rate of icariin in scheme 2 was about 18% higher than that in scheme 1. It indicates that, in the process of Shengbai mixture (oral solution) production, mixing the extract well with ethanol at the ratio of 1:1-1.2 first, then adding ethanol to alcohol content of 70% can increase the content of icariin in Shengbai extract, about 18% higher than that in Scheme 1.

3. The Influence of Different Times of Adjusting pH on the Content of Icariin, Clarity and Taste of the Finished Product During the Production and Preparation of Shengbai Mixture (Oral Solution).

3.1 Experimental Schemes 3.1.1 Experimental scheme (1): Based on the production process, taking 100 g of the Shengbai extract (extract density 1.26) of embodiment 1, adding purified water and steviosin, stirring, heating to boiling for 30 min, refrigerating for 48 h, taking the supernatant, adjusting pH value to 7.0, adjusting the volume to required level, filtering, filling, then sterilizing. The next day, observing the clarity of the oral solution, detecting its pH, tasting, and detecting the content of icariin in the finished product.

3.1.2 Experimental scheme (2): Based on the production process, taking 100 g of the Shengbai extract (extract density 1.26) of embodiment 1, adding purified water and steviosin, stirring, adjusting pH value to 5.3, heating to boiling for 30 min, refrigerating for 48 h, taking the supernatant, adjusting pH value to 7.0, adjusting the volume to required level, filtering, filling, then sterilizing. The next day, observing the clarity of the oral solution, detecting its pH, tasting, and detecting the content of icariin in the finished product.

Note: Except for the change of times of adjusting pH, the other technical parameters remained unchanged.

3.2 Experimental Results and Analysis 3.2.1 Experimental Results

TABLE 9

| — | Scheme | Concentration of icariin in the finished product (mg/ml) | pH value of the finished product after sterilization | Taste | Clarity |
|---|---|---|---|---|---|
| Detection 1-1 | (1) | 2.0 | 6.1 | Slightly bitter, astringent | Slightly turbid, with a small amount of sediment at bottom |
| Detection 1-2 | (1) | 1.9 | 6.3 | Slightly bitter, astringent | Slightly turbid, with a small amount of sediment at bottom |
| Detection 1-3 | (1) | 2.0 | 6.2 | Slightly bitter, astringent | Slightly turbid, with a small amount of sediment at bottom |
| Detection 2-1 | (2) | 2.3 | 5.8 | Slightly bitter, not astringent | Clear, without sediment at bottom |
| Detection 2-2 | (2) | 2.2 | 5.8 | Slightly bitter, not astringent | Clear, without sediment at bottom |
| Detection 2-3 | (2) | 2.3 | 5.9 | Slightly bitter, not astringent | Clear, without sediment at bottom |

3.2.2 Analysis of Experimental Results

Data of detection 1-1, 1-2 and 1-3 belong to scheme 1, data of detection 2-1, 2-2 and 2-3 belong to scheme 2, the concentration of icariin in scheme 2 was a little higher than that in scheme 1, taste and clarity thereof were better as well. It indicates that, in the process of Shengbai mixture (oral solution) production, adjusting pH twice can increase the concentration of icariin in the finished product, improve the taste and clarity of the oral solution.

Example 4 Comparison of Fingerprints Before and after Process Modification of Shengbai Oral Solution 1. Standard for Fingerprint Detection of Shengbai Oral Solution

[fingerprint] Detect according to HPLC method (CP 2015, Volume IV, General Chapter 0512).

Using octadecylsilane chemically bonded silica as filler (column length 25 cm, inner diameter 4.6 mm, particle size 5 μm); acetonitrile as mobile phase A and 0.1% formic acid as mobile phase B, conducting gradient elution based on the following table; detection wavelength 270 nm; column temperature 30° C.; flow rate 1.0 ml/min; theoretical plate number not less than 10000 calculated based on icariin peak.

TABLE 10

Table of gradient elution, fingerprint detection of Shengbai oral solution

| Time(min) | Mobile phase A(%) | Mobile phase B(%) |
|---|---|---|
| 0~10 | 2→6 | 98→94 |
| 10~31 | 6→23 | 94→77 |
| 31~40 | 23→26 | 77→74 |
| 40~56 | 26→53 | 74→47 |
| 56~60 | 53→80 | 47→20 |
| 60~70 | 80→80 | 20→20 |

Preparation of reference solution An appropriate amount of icariin reference standards were accurately weighed and prepared into a solution of 100 μg/ml, which was shaken well to obtain the reference solution.

Preparation of test solution 2 ml of the product was accurately measured, transferred into a 10 ml flask, diluted with water to scale, shaken well, filtered to get the subsequent filtrate as the test solution.

Test method 10 μl each of the reference solution and test solution were accurately taken, then injected into the liquid chromatograph to record the chromatogram for 70 minutes.

Original process: CN201410701679.7

Current process: Embodiment 1

Conclusion: As shown in Table 11, data comparison before and after the above process modification demonstrated that, after the modification, total area of the 14 common peaks increased from 18265009 to 22574539 (percentage increased by 23.6%), indicating the content of active chemical substances in the product increased by 23.6%.

TABLE 11

Total peak area comparison of chemical substances before and after the process modification

| | Shengbai oral solution | | | Original process | Current process |
|---|---|---|---|---|---|
| Serial number | Chemical substance | Retention time | Peak attribution | (CN201410701679.7) Peak area | (Embodiment 1) Peak area |
| 1 | Leucine | 8.439 | Fructus Lycii, Radix Rubiae, Radix Angelicae Sinensis | 1137729 | 1331287 |
| 2 | Guanosine | 10.397 | Radix Astragali, Radix Angelicae Sinensis | 277256 | 428019 |
| 3 | Psoralenoside | 32.081 | Fructus Psoraleae | 954407 | 1912896 |
| 4 | Isopsoralenoside | 32.878 | Fructus Psoraleae | 577937 | 1488798 |
| 5 | Calycosin-7-glucoside | 35.172 | Calycosin-7-glucoside | 714367 | 876501 |
| 6 | Liquiritin | 36.522 | Radix et Rhizoma Glycyrrhizae(Liquiritin) | 938276 | 1466893 |
| 7 | Icariin A | 42.709 | Folium Epimedii | 449605 | 632233 |
| 8 | 1,3-dihydroxyl-2-hydroxy methylanthraquinone | 47.889 | Radix Rubiae | 1199892 | 1411033 |
| 9 | Epimedin A | 49.113 | Epimedin A | 713382 | 671931 |
| 10 | Epimedin B | 49.578 | Epimedin B | 1320262 | 1393452 |
| 11 | Epimedin C | 49.992 | Epimedin C | 2699327 | 2993842 |
| 12 | Icariin | 50.738 | Icariin | 5786684 | 6210262 |
| 13 | 1,3,6-trihydroxy-2-methyl anthraquinone | 53.367 | Radix Rubiae | 952917 | 1076187 |
| 14 | Glycyrrhizic acid | 58.009 | Glycyrrhizic acid | 542968 | 681205 |
| | | | Total peak area | 18265009 | 22574539 |

DETAILED DESCRIPTION OF THE INVENTION

Figure 1:
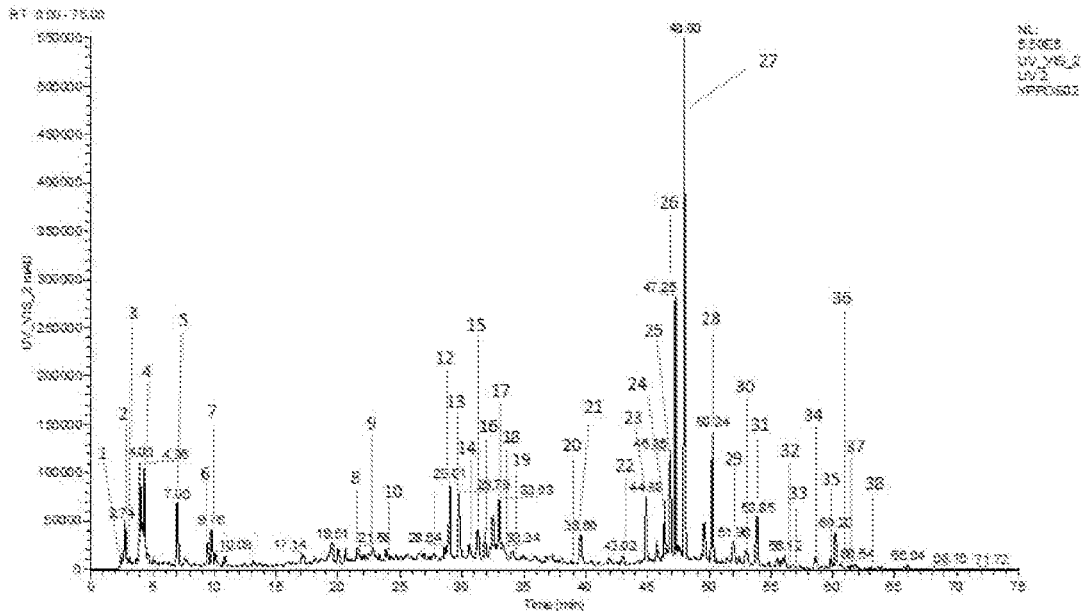
FIG. 1 is the HPLC chromatogram based on HPLC-ESI-MS of Shengbai oral solution of the invention.

The specific embodiments of the invention are described in combination with the attached drawings, but are not construed as a limitation of the invention.

Unless otherwise expressly stated, the terms "include" or "including" throughout the specifications and claims will be construed to include the elements or components stated, without excluding other elements or components.

Embodiment 1

Step (1): Taking 240 g of Folium Epimedii, 120 g of Fructus Psoraleae, 80 g of Radix Aconiti Lateralis Preparata (Processed), 240 g of Fructus Lycii, 240 g of Radix Astragali, 240 g of Caulis Spatholobi, 240 g of Radix Rubiae, 120 g of Radix Angelicae Sinensis, 240 g of Rhizoma Phragmitis, 120 g of Radix Ophiopogonis and 120 g of Radix et Rhizoma Glycyrrhizae, standby;

Step (2): Adding water into the above formulated amount of 10 kinds of prepared slices of Chinese crude drugs of the invention first (not including Folium Epimedii) and heating at 75-80° C. to boiling, then adding formulated amount of Folium Epimedii, continuing heating at 75-80° C. to boiling, extracting for 1 h, then filtering to get the filtrate once, adding water to the residues for a second-time extraction, filtering to get the filtrate once again, combining the two-time filtrates, concentrating to relative density of 1.24-1.27 (25±5° C.) to obtain extract I;

Step (3): Slowly adding 90% ethanol into extract I of the invention at the ratio of extract I:ethanol=1:1-1.2, adding while stirring, so that extract I could be evenly dispersed, and then adding 90% ethanol to alcohol content of 70%, adding while stirring, standing for 72 h for alcohol precipitation, filtering, recovering ethanol, concentrating to relative density of 1.24-1.27 (25±5° C.) to obtain the Shengbai extract, which is the drug of the invention;

Step (4): Taking 100 g of the Shengbai extract (extract density 1.26), adding purified water and steviosin based on the production process, stirring, adjusting pH value to 5.3 with sodium hydroxide, heating to boiling for 30 min, refrigerating for 48 h, taking the supernatant, adjusting pH value to 7.0 with sodium hydroxide, adjusting the volume to required level, filtering, filling, then sterilizing.

Embodiment 2

Step (1): Taking 200 g of Folium Epimedii, 100 g of Fructus Psoraleae, 60 g of Radix Aconiti Lateralis Preparata (Processed), 200 g of Fructus Lycii, 200 g of Radix Astragali, 200 g of Caulis Spatholobi, 200 g of Radix Rubiae, 100 g of Radix Angelicae Sinensis, 200 g of Rhizoma Phragmitis, 100 g of Radix Ophiopogonis and 100 g of Radix et Rhizoma Glycyrrhizae, standby;

Step (2): Adding water into the above formulated amount of 10 kinds of prepared slices of Chinese crude drugs of the invention first (not including Folium Epimedii) and heating at 80-85° C. to boiling, then adding formulated amount of Folium Epimedii, continuing heating at 80-85° C. to boiling, extracting for 1 h, then filtering to get the filtrate once, adding water to the residues for a second-time extraction, filtering to get the filtrate once again, combining the two-time filtrates, concentrating to relative density of 1.24-1.27 (25±5° C.) to obtain extract I;

Step (3): Slowly adding 90% ethanol into extract I of the invention at the ratio of extract I:ethanol=1:1-1.2, adding while stirring, so that extract I could be evenly dispersed, and then adding 90% ethanol to alcohol content of 70%, adding while stirring, standing for 72 h for alcohol precipitation, filtering, recovering ethanol, concentrating to relative density of 1.24-1.27 (25±5° C.) to obtain the Shengbai extract.

Embodiment 3

Step (1): Taking 300 g of Folium Epimedii, 160 g of Fructus Psoraleae, 120 g of Radix Aconiti Lateralis Preparata (Processed), 300 g of Fructus Lycii, 300 g of Radix Astragali, 300 g of Caulis Spatholobi, 300 g of Radix Rubiae, 160 g of Radix Angelicae Sinensis, 300 g of Rhizoma Phragmitis, 160 g of Radix Ophiopogonis and 160 g of Radix et Rhizoma Glycyrrhizae, standby;

Step (2): Adding water into the above formulated amount of 10 kinds of prepared slices of Chinese crude drugs of the invention first (not including Folium Epimedii) and heating at 90-100° C. to boiling, then adding formulated amount of Folium Epimedii, continuing heating at 90-100° C. to boiling, extracting for 1 h, then filtering to get the filtrate once, adding water to the residues for a second-time extraction, filtering to get the filtrate once again, combining the two-time filtrates, concentrating to relative density of 1.24-1.27 (25±5° C.) to obtain extract I;

Step (3): Slowly adding 90% ethanol into extract I of the invention at the ratio of extract I:ethanol=1:1-1.2, adding while stirring, so that extract I could be evenly dispersed, and then adding 90% ethanol to alcohol content of 70%, adding while stirring, standing for 72 h for alcohol precipitation, filtering, recovering ethanol, concentrating to relative density of 1.24-1.27 (25±5° C.) to obtain the Shengbai extract.

Embodiment 4

Step (1): Taking 240 g of Folium Epimedii, 120 g of Fructus Psoraleae, 80 g of Radix Aconiti Lateralis Preparata (Processed), 240 g of Fructus Lycii, 240 g of Radix Astragali, 240 g of Caulis Spatholobi, 240 g of Radix Rubiae, 120 g of Radix Angelicae Sinensis, 240 g of Rhizoma Phragmitis, 120 g of Radix Ophiopogonis and 120 g of Radix et Rhizoma Glycyrrhizae, standby;

Step (2): Adding water into the above formulated amount of 10 kinds of prepared slices of Chinese crude drugs of the invention first (not including Folium Epimedii) and heating at 75-80° C. to boiling, then adding formulated amount of Folium Epimedii, continuing heating at 75-80° C. to boiling, extracting for 0.5 h, then filtering to get the filtrate once, adding water to the residues for a second-time extraction, filtering to get the filtrate once again, combining the two-time filtrates, concentrating to relative density of 1.24-1.27 (25±5° C.) to obtain extract I;

Step (3): Slowly adding 95% ethanol into extract I of the invention at the ratio of extract I:ethanol=1:1-1.2, adding while stirring, so that extract I could be evenly dispersed, and then adding 95% ethanol to alcohol content of 75%, adding while stirring, standing for 36 h for alcohol precipitation, filtering, recovering ethanol, concentrating to relative density of 1.24-1.27 (25±5° C.) to obtain the Shengbai extract.

Embodiment 5

Step (1): Taking 240 g of Folium Epimedii, 120 g of Fructus Psoraleae, 80 g of Radix Aconiti Lateralis Preparata (Processed), 240 g of Fructus Lycii, 240 g of Radix Astragali, 240 g of Caulis Spatholobi, 240 g of Radix Rubiae, 120 g of Radix Angelicae Sinensis, 240 g of Rhizoma Phragmitis, 120 g of Radix Ophiopogonis and 120 g of Radix et Rhizoma Glycyrrhizae, standby;

Step (2): Adding water into the above formulated amount of 10 kinds of prepared slices of Chinese crude drugs of the invention first (not including Folium Epimedii) and heating at 100° C. to boiling, then adding formulated amount of Folium Epimedii, continuing heating at 100° C. to boiling, extracting for 1.5 h, then filtering to get the filtrate once, adding water to the residues for a second-time extraction, filtering to get the filtrate once again, combining the two-time filtrates, concentrating to relative density of 1.24-1.27 (25±5° C.) to obtain extract I;

Step (3): Slowly adding absolute ethanol into extract I of the invention at the ratio of extract 1:ethanol=1:1-1.2, adding while stirring, so that extract I could be evenly dispersed, and then adding absolute ethanol to alcohol content of 80%, adding while stirring, standing for 60 h for alcohol precipitation, filtering, recovering ethanol, concentrating to relative density of 1.24-1.27 (25±5° C.) to obtain the Shengbai extract.

Embodiment 6. A Shengbai Oral Solution

Taking 100 g of Shengbai extract (extract density 1.26) of embodiment 2, adding purified water and 0.2% steviosin, stirring, adjusting pH value to 5.3 with sodium bicarbonate, heating to boiling for 30 min, refrigerating for 48 h, taking the supernatant, adjusting pH value to 7.0 with sodium bicarbonate, adjusting the volume to required level, filtering, filling, then sterilizing.

Embodiment 7. A Shengbai Oral Solution

Taking 100 g of Shengbai extract (extract density 1.26) of any of embodiments 1-5, adding purified water and 0.2% steviosin, stirring, adjusting pH to 5.5 with sodium bicarbonate, heating to boiling for 30 min, refrigerating for 48 h, taking the supernatant, adjusting pH to 7.3 with sodium hydroxide, adjusting the volume to required level, filtering, filling, then sterilizing.

Embodiment 8. A Shengbai Oral Solution

Taking 100 g of Shengbai extract (extract density 1.26) of any of embodiments 1-5, adding purified water and 0.5% white granulated sugar, stirring, adjusting pH to 6.0, heating to boiling for 30 min, refrigerating for 48 h, taking the supernatant, adjusting pH to 7.5, adjusting the volume to required level, filtering, filling, then sterilizing.

Embodiment 9. A Shengbai Oral Solution

Taking 100 g of Shengbai extract (extract density 1.26) of any of embodiments 1-5, adding purified water and 0.5% white granulated sugar, stirring, adjusting pH to 5.0, heating to boiling for 30 min, refrigerating for 48 h, taking the supernatant, adjusting pH to 6.5, adjusting the volume to required level, filtering, filling, then sterilizing.

Embodiment 10. A Shengbai Granule

Taking 100 g of Shengbai extract of any of embodiments 1-5, 24 g of cyclodextrin, 16 g of sodium carboxymethyl starch, 21 g of lactose, 0.67 g of steviosin, 9.5 g of citric acid (effervescing agent), 3.1 g of sodium bicarbonate and 6.2 g of sodium carbonate, fully mixing well, conducting dry granulation and granule screening to obtain Shengbai granules.

Embodiment 11. A Shengbai Capsule

Taking 100 g of Shengbai extract of any of embodiments 1-5, adding 110 g of calcium carbonate and 20 g of starch, mixing, drying, grinding into fine powders, screening, mixing well, encapsulating into 1000 capsules.

Embodiment 12. A Shengbai Chewable Tablet

Taking 100 g of Shengbai extract of any of embodiments 1-5, modifying with dextrin, then conducting spray drying, grinding into fine powders, adding sucrose, dextrin, mannitol, flavoring agents and other excipients, carrying out spray granulation, drying at 60° C., adding appropriate amount of magnesium stearate, tabletting into 1000 chewable tablets.

Embodiment 13. A Shengbai Suspension

Taking 100 g of Shengbai extract of any of embodiments 1-5, 16 g of sodium hydroxide, 50 g of sodium citrate, 29 g of citric acid, 400 ml of simple syrup, 10 ml of 4% ethylparaben solution, adding distilled water to 100 ml to obtain the suspension.

Embodiment 14. A Shengbai Granule

Taking 10 g of Shengbai extract of any of embodiments 1-5, 40 g of sucrose, adding 50% ethanol (wetting agent) to prepare into granules according to the method of preparing granules.

Embodiment 15. A Shengbai Tablet

Taking 100 g of Shengbai extract of any of embodiments 1-5, 1 g of microcrystalline cellulose, adding 95% ethanol to prepare into tablets according to the method of preparing tablets.

Embodiment 16. Preparation of Dry Extract Powder (1) Spray Drying

Step (1): Taking 240 g of Folium Epimedii, 120 g of Fructus Psoraleae, 80 g of Radix Aconiti Lateralis Preparata, 240 g of Fructus Lycii, 240 g of Radix Astragali, 240 g of Caulis Spatholobi, 240 g of Radix Rubiae, 120 g of Radix Angelicae Sinensis, 240 g of Rhizoma Phragmitis, 120 g of Radix Ophiopogonis and 120 g of Radix et Rhizoma Glycyrrhizae, standby;

Step (2): Adding water into the above formulated amount of 10 kinds of prepared slices of Chinese crude drugs of the invention first (not including Folium Epimedii) and heating to 75-80° C., then adding formulated amount of Folium Epimedii, continuing heating to boiling, extracting for 1 h, then filtering to get the filtrate once, adding water to the residues for a second-time extraction, filtering to get the filtrate once again, combining the two-time filtrates, concentrating to relative density of 1.24-1.27 (25±5° C.) to obtain extract I;

Step (3): Slowly adding 90% ethanol into extract I at the ratio of extract I:ethanol=1:1-1.2, adding while stirring, so that extract I could be evenly dispersed, and then adding 90% ethanol to alcohol content of 70%, adding while stirring, standing for 72 h for alcohol precipitation, filtering, recovering ethanol, concentrating to relative density of 1.10-1.12 (50° C.) to obtain extract II;

Step (4): Adding 80 g of β-cyclodextrin and 80 g of dextrin to extract II, stirring at 60° C. for 30 min, carrying out spray drying, with inlet air temperature at 150-170° C., outlet air temperature at 75-90° C., atomizer speed at 280 Hz, liquid inlet speed at 12 Hz, obtaining dry extract powder I of 400 g±5%, with moisture of 4-6%.

(2) Microwave Vacuum Drying

Step (1): Taking 240 g of Folium Epimedii, 120 g of Fructus Psoraleae, 80 g of Radix Aconiti Lateralis Preparata, 240 g of Fructus Lycii, 240 g of Radix Astragali, 240 g of Caulis Spatholobi, 240 g of Radix Rubiae, 120 g of Radix Angelicae Sinensis, 240 g of Rhizoma Phragmitis, 120 g of Radix Ophiopogonis and 120 g of Radix et Rhizoma Glycyrrhizae, standby;

Step (2): Adding water into the above formulated amount of 10 kinds of prepared slices of Chinese crude drugs of the invention first (not including Folium Epimedii) and heating to 75-80° C., then adding formulated amount of Folium Epimedii, continuing heating to boiling, extracting for 1 h, then filtering to get the filtrate once, adding water to the residues for a second-time extraction, filtering to get the filtrate once again, combining the two-time filtrates, concentrating to relative density of 1.24-1.27 (25±5° C.) to obtain extract I;

Step (3): Slowly adding 90% ethanol into extract I at the ratio of extract I:ethanol=1:1-1.2, adding while stirring, so that extract I could be evenly dispersed, and then adding 90% ethanol to alcohol content of 70%, adding while stirring, standing for 72 h for alcohol precipitation, filtering, recovering ethanol, concentrating to relative density of 1.24-1.27 (50° C.) to obtain extract II;

Step (4): Adding 80 g of β-cyclodextrin and 80 g of dextrin to extract II, stirring at 60° C. for 30 min, drying with the microwave vacuum drying oven, with the drying temperature at 50-60° C., obtaining dry extract powder I of 400 g±5%, with moisture of 4-6%.

Embodiment 17. Granules (Dry Granulation)

Step (1): Adding 1 g of steviosin (flavoring agent) and 20 g of sodium carboxymethyl starch (disintegrant) to the dry extract powder I of embodiment 15, fully mixing well, carrying out dry granulation at 18-60° C. and granule screening to get the granules, packing into 9 g/bag to obtain the product.

Embodiment 18. Granules (One-Step Granulation)

Step (1): After screening, adding the dry extract powder I of embodiment 15.1 g of steviosin (flavoring agent) and 20 g of sodium carboxymethyl starch (disintegrant) respectively into the fluid bed granulator of the fluid bed drying granulating machine, with the inlet hot air temperature at 70-80° C., to make the solid materials boil, premix and preheat for about 20 minutes. After qualified preheating (i.e. material temperature over 60° C.), spraying the purified water into the granulator through a spray gun for boiling drying granulation, then collecting dry granules. When spraying, the inlet air temperature: 70-90° C., the outlet air temperature: 60-70° C., peristaltic pump speed: 50-150 rpm. After spraying, continuing supplying air (with the temperature maintained at 60-70° C.) for about 20-30 minutes to control the granule moisture within the range of not more than 4%. Collecting and screening to get the granules, packing into 9 g/bag to obtain the product.

Embodiment 19. Tablets

Step (1): After screening, adding the dry extract powder I of embodiment 15.1 g of steviosin (flavoring agent) and 20 g of sodium carboxymethyl starch (disintegrant) respectively into the fluid bed granulator of the fluid bed drying granulating machine, with the inlet hot air temperature at 70-80° C., to make the solid materials boil, premix and preheat for about 20 minutes. After qualified preheating (i.e. material temperature over 60° C.), spraying the purified water into the granulator through a spray gun for boiling drying granulation, then collecting dry granules. When spraying, the inlet air temperature: 70-90° C., the outlet air temperature: 60-70° C., peristaltic pump speed: 50-150 rpm. After spraying, continuing supplying air (with the temperature maintained at 60-70° C.) for about 20-30 minutes to make the granule moisture not more than 4%. Collecting and screening granules, adding 3% magnesium stearate and 3 g of sodium bicarbonate, mixing well, tabletting into 0.9 g/tablet to obtain the product.

Embodiment 20. Capsules

Step (1): After screening, adding the dry extract powder I of embodiment 15.1 g of steviosin (flavoring agent) and 20 g of sodium carboxymethyl starch (disintegrant) respectively into the fluid bed granulator of the fluid bed drying granulating machine, with the inlet hot air temperature at 70-80° C., to make the solid materials boil, premix and preheat for about 20 minutes. After qualified preheating (i.e. material temperature over 60° C.), spraying the purified water into the granulator through a spray gun for boiling drying granulation, then collecting dry granules. When spraying, the inlet air temperature: 70-90° C., the outlet air temperature: 60-70° C., peristaltic pump speed: 50-150 rpm. After spraying, continuing supplying air (with the temperature maintained at 60-70° C.) for about 20-30 minutes to make the granule moisture not more than 4%. Collecting and screening granules, adding 3 g of sodium bicarbonate, mixing well, encapsulating into 0.9 g/capsule to obtain the product.

Embodiment 21. Pills

Step (1): Adding sodium carboxymethyl starch (disintegrant) to the dry extract powder I of embodiment 15, fully mixing well, adding purified water to make soft materials, then preparing into concentrated pills, drying to 0.8 g/pill to obtain the product.

Embodiment 22. Preparation of Fluid Extract

Step (1): Taking 240 g of Folium Epimedii, 120 g of Fructus Psoraleae, 80 g of Radix Aconiti Lateralis Preparata, 240 g of Fructus Lycii, 240 g of Radix Astragali, 240 g of Caulis Spatholobi, 240 g of Radix Rubiae, 120 g of Radix Angelicae Sinensis, 240 g of Rhizoma Phragmitis, 120 g of Radix Ophiopogonis and 120 g of Radix et Rhizoma Glycyrrhizae, standby;

Step (2): Adding water into the above formulated amount of 10 kinds of prepared slices of Chinese crude drugs of the invention first (not including Folium Epimedii) and heating to 75-80° C., then adding formulated amount of Folium Epimedii, continuing heating to boiling, extracting for 1 h, then filtering to get the filtrate once, adding water to the residues for a second-time extraction, filtering to get the filtrate once again, combining the two-time filtrates, concentrating to relative density of 1.24-1.27 (25±5° C.) to obtain extract I;

Step (3): Slowly adding 90% ethanol into extract I at the ratio of extract I:ethanol=1:1-1.2, adding while stirring, so that extract I could be evenly dispersed, and then adding 90% ethanol to alcohol content of 70%, adding while stirring, standing for 72 h for alcohol precipitation, filtering, recovering ethanol, concentrating to relative density of 1.24-1.27 (50° C.) to obtain extract II.

Embodiment 23. Syrups

Step (1): Taking 650 g of sucrose, boiling with water to make syrup, mixing well with the fluid extract II of embodiment 22, boiling, cooling to 40° C., adding 2 g of sodium benzoate, adjusting pH to 6-7, adding water to 1000 ml, stirring well, standing, filtering, filling to get the product.

Embodiment 24. Pastes

Step (1): Adding appropriate amount of sucrose into the fluid extract II of embodiment 22 (200 g of sucrose per 100 g of extract II), heating to melt, mixing well, concentrating to relative density of 1.30-1.35 (25° C.), filling to get the product.

Embodiment 25. Analysis of Chemical Constituents of Shengbai Oral Solution Fingerprint 1. Instruments Chromatograph: Dionex Ultimate 3000 RSLC (HPG) HPLC system (automatic sampler, dual trinary pump, column oven, in-line degassing unit and DAD detector);

Chromatographic column: Kromasil 100-5-C18 column (250 mm×4.6 mm, 5 μm).

Mass spectrometer: Thermo Scientific Q Exactive Series system (sample injection system, HESI-II ion source, mass analyzer, TraceFinder data processing system).

2. Reagents

Acetonitrile: Chromatographically pure, supplied by Fisher Chemical;

Methanol: Chromatographically pure, supplied by Tianjin Kemiou Chemical Reagent Co., Ltd.;

Water: Watsons distilled water.

3. Chromatographic Conditions

Using octadecylsilane chemically bonded silica as filler (column length 25 cm, inner diameter 4.6 mm, particle size 5 μm); acetonitrile as mobile phase A and 0.1% formic acid as mobile phase B, conducting gradient elution based on the following table; flow rate 1.0 ml/min; column temperature 30° C.; detection wavelength 270 nm; sample size 10 μL; sample plate temperature 25° C.

| Gradient elution table | | |
| --- | --- | --- |
| Time (min) | Mobile phase A (%) | Mobile phase B (%) |
| 0~10 | 2→6 | 98→94 |
| 10~31 | 6→23 | 94→77 |
| 31~40 | 23→26 | 77→74 |
| 40~56 | 26→53 | 74→47 |

-continued

Gradient elution table

| Time (min) | Mobile phase A (%) | Mobile phase B (%) |
|---|---|---|
| 56~60 | 53→80 | 47→20 |
| 60~70 | 80→80 | 20→20 |
| 70~75 | 80→2 | 20→98 |

4. Mass Spectrometry Conditions

Atmosphere electrospray ionization source (ESI), positive and negative ion scanning, Full MS-ddms2 scan mode; Scan range: 100-1500 m/z; Resolution: Full MS: 70,000; MS/MS: 17,500; Capillary voltage: 3.0 kv for positive ion scanning mode, 2.5 kv for negative ion scanning mode; Sheath gas pressure: 30 bar; Aux gas pressure: 10 bar; Capillary temperature: 320° C.; Atomized gas temperature: 350° C.; Compound stability: 100%; NCE: 30.

5. Results and Discussion 5.1 HPLC-ESI-MS Analysis of Shengbai Oral Solution

Figure 2:
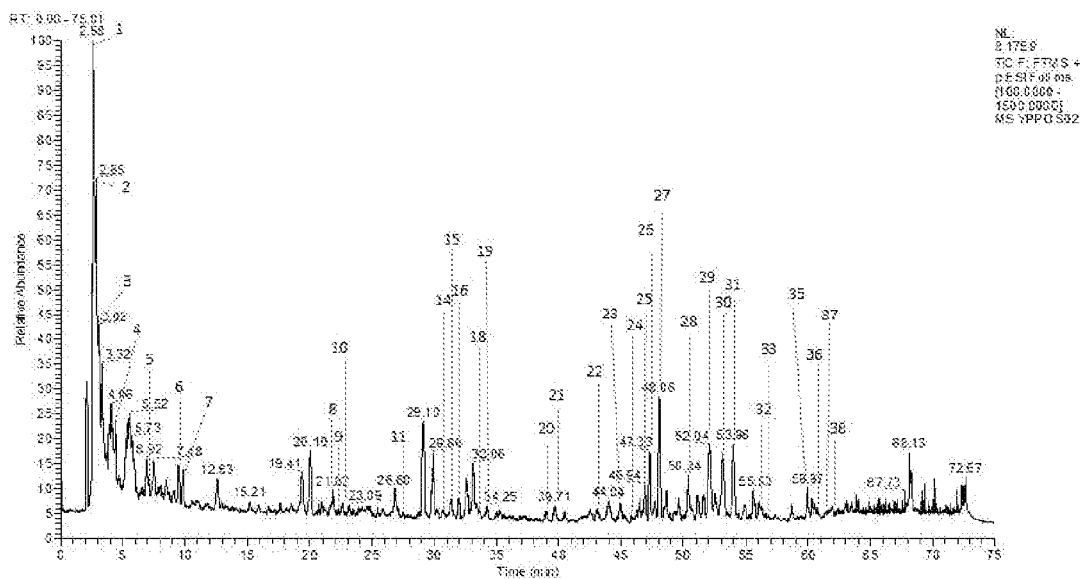
FIG. 2 is the total ion chromatogram (positive ion mode) based on HPLC-ESI-MS of Shengbai oral solution of the invention.
Figure 3:
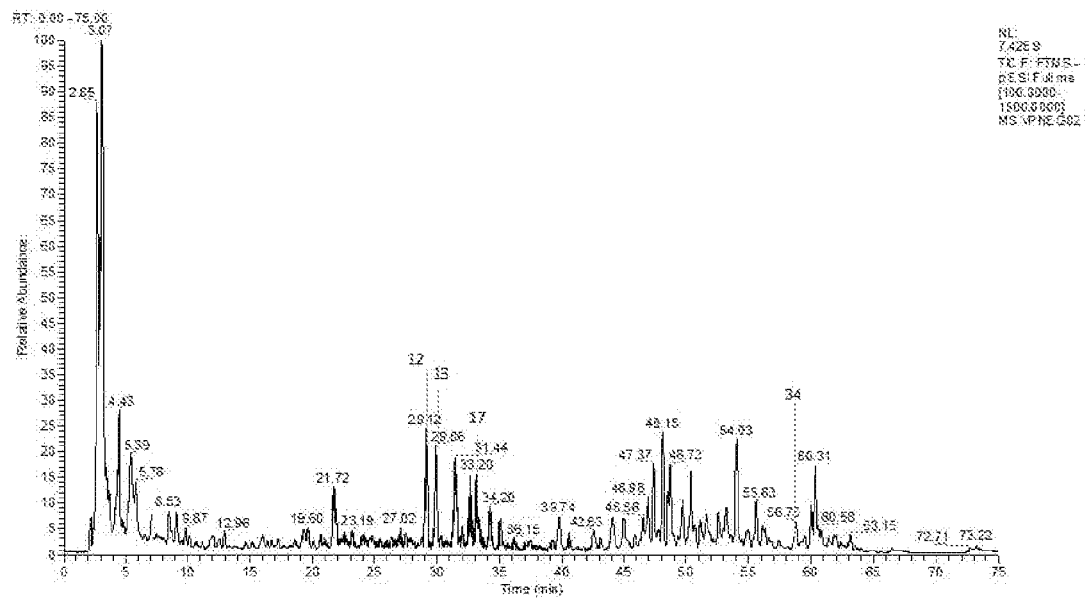
FIG. 3 is the total ion chromatogram (negative ion mode) based on HPLC-ESI-MS of Shengbai oral solution of the invention.
Figure 4:
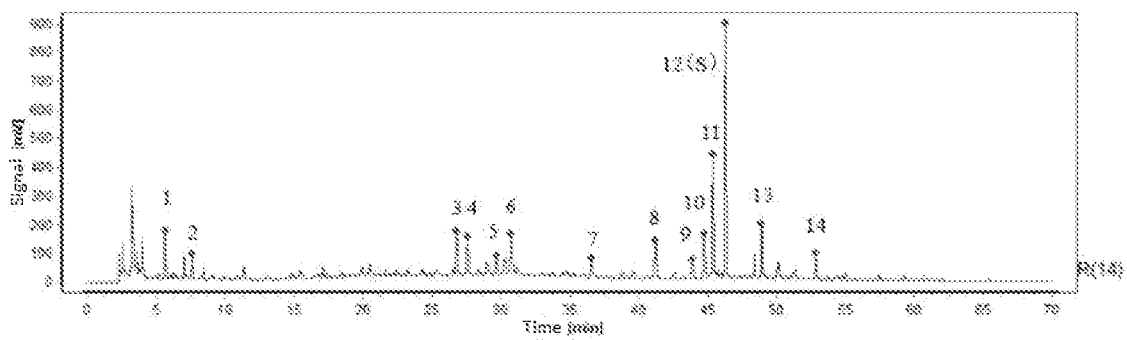
FIG. 4 is the HPLC chromatogram of the drug of the invention (14 common peaks).

Under the condition of LC-MS, obvious [M+H]$^+$ or [M−H]$^−$ signals were observed in the liquid chromatogram, the total ion chromatogram (both positive and negative ion scanning modes) of mass spectrometry of test samples. ESI-MS data as shown in Table 12 and FIG. 1-3.

Embodiment 26. Determination of Common Peaks of Shengbai Oral Solution

1. Instruments and Materials

Chromatograph: USA Waters e2695 LC system (Waters PDA detector, Empower 3 workstation);

Chromatographic column: Kromasil 100-5 C18 column (250 mm×4.6 mm, 5 μm);

Reagents:

Ethanol, analytically pure, supplied by Beijing Chemical Works;

Acetonitrile, chromatographically pure, supplied by Tianjin Fuyu Fine Chemical Co., Ltd.;

Formic acid, supplied by Tianjin Kemiou Chemical Reagent Co., Ltd.;

Purified water, supplied by Hangzhou Wahaha Group Co., Ltd.;

Adenosine (lot number CHB170802), supplied by Chengdu Chroma-Biotechnology Co., Ltd.;

Calycosin-7-glucoside (lot number 111920-201505), supplied by National Institutes for Food and Drug Control;

Liquiritin (lot number 11160-201106), supplied by National Institutes for Food and Drug Control;

Glycyrrhizic acid (lot number 110731-201418), supplied by National Institutes for Food and Drug Control;

TABLE 12

ESI-MS data of Shengbai oral solution

| No. | Time (min) | Common peak | Name | [M + H]$^+$ | [M − H]$^−$ | HPLC/ESI-MS m/z |
|---|---|---|---|---|---|---|
| 1 | 2.58 | | Glutamic acid | 148 | | MS2[148 → 130, 84] |
| 2 | 2.87 | | Proline | 116 | | MS2[116 → 70] |
| 3 | 3.04 | | 5-hydroxymethylfurfural | 127 | | MS2[127 → 109] |
| 4 | 4.70 | | Nicotinic acid | 124 | | MS2[124 → 79] |
| 5 | 6.96 | 1 | Leucine | 132 | | MS2[132 → 86] |
| 6 | 9.50 | | Adenosine | 268 | | MS2[268 → 136] |
| 7 | 9.76 | 2 | Guanosine | 284 | | MS2[284 → 152] |
| 8 | 21.84 | | Senkyunolide A | 193 | | MS2[193 → 91] |
| 9 | 22.44 | | Songorine | 358 | | MS2[358 → 340] |
| 10 | 24.54 | | Fuziline | 454 | | MS2[454 → 436] |
| 11 | 27.72 | | p-hydroxy benzaldehyde | 123 | | MS2[123 → 95] |
| 12 | 29.12 | 3 | Psoralenoside | | 365 | MS2[365 → 203, 159] |
| 13 | 29.86 | 4 | Isopsoralenoside | | 365 | MS2[365 → 203, 159] |
| 14 | 30.92 | | Vanillin | 153 | | MS2[153 → 125] |
| 15 | 31.32 | | p-hydroxy-cinnamic acid | 165 | | MS2[165 → 147] |
| 16 | 31.95 | 5 | Calycosin-7-glucoside | 447 | | MS2[447 → 285] |
| 17 | 33.20 | 6 | Liquiritin | | 417 | MS2[417 → 255, 135] |
| 18 | 33.59 | | Ferulic acid | 195 | | MS2[195 → 177, 145] |
| 19 | 34.24 | | Catechin | 291 | | MS2[291 → 245, 227] |
| 20 | 39.01 | | Benzoylmesaconine | 590 | | MS2[590 → 540] |
| 21 | 39.60 | 7 | Icariin A | 663 | | MS2[663 → 355] |
| 22 | 43.13 | | Ononin | 431 | | MS2[431 → 269] |
| 23 | 44.88 | 8 | 1,3-dihydroxyl-2-hydroxy methylanthraquinone | 271 | | MS2[271 → 215] |
| 24 | 46.52 | 9 | Epimedin A | 839 | | MS2[839 → 369] |
| 25 | 46.94 | 10 | Epimedin B | 809 | | MS2[809 → 369] |
| 26 | 47.33 | 11 | Epimedin C | 823 | | MS2[823 → 369] |
| 27 | 48.13 | 12 | Icariin | 677 | | MS2[677 → 369, 313] |
| 28 | 50.24 | 13 | 1,3,6-trihydroxy-2-methylanthraquinone | 271 | | MS2[271 → 255] |
| 29 | 52.04 | | Psoralen | 187 | | MS2[187 → 143] |
| 30 | 53.11 | | Isopsoralen | 187 | | MS2[187 → 143] |
| 31 | 53.95 | 14 | Glycyrrhizic acid | 823 | | MS2[823 → 453] |
| 32 | 56.38 | | Ligustilide | 191 | | MS2[191 → 173] |
| 33 | 56.80 | | Icarisid I | 531 | | MS2[531 → 369, 313] |
| 34 | 58.73 | | Baohuoside I | | 513 | MS2[513 → 366, 323] |
| 35 | 59.92 | | Neobavaisoflavone | 323 | | MS2[323 → 267] |
| 36 | 60.73 | | Bavachin | 325 | | MS2[325 → 269] |
| 37 | 61.38 | | Bavachinin | 339 | | MS2[339 → 283] |
| 38 | 63.09 | | Isobavachalcone | 325 | | MS2[325 → 269] |

Epimedin A (lot number MUST-16072304), supplied by Chengdu Must Biotechnology Co., Ltd.;

Epimedin B (lot number MUST-15121410), supplied by Chengdu Must Biotechnology Co., Ltd.;

Epimedin C (lot number 111780-201503), supplied by National Institutes for Food and Drug Control;

Icariin (lot number 110737-201516), supplied by National Institutes for Food and Drug Control;

Psoralen (lot number MUST-17092820), supplied by Chengdu Chroma-Biotechnology Co., Ltd.;

Isopsoralen (lot number MUST-18062910), supplied by Chengdu Chroma-Biotechnology Co., Ltd.;

Psoralenoside (lot number DST180723-923), supplied by Chengdu Desite Biotechnology Co., Ltd.;

Isopsoralenoside (lot number DST180723-924), supplied by Chengdu Desite Biotechnology Co., Ltd.

Test samples: Prepared according to embodiment 1, supplied by Hubei Monyan Pharmaceutical Co., Ltd., details as shown in Table 13.

TABLE 13

Test samples for fingerprint study of Shengbai oral solution

| Name | Lot number | Specification |
|---|---|---|
| Shengbai oral solution | 160302 | 20 ml/vial |
| | 160303 | 20 ml/vial |
| | 160304 | 20 ml/vial |
| | 170603 | 20 ml/vial |
| | 170902 | 20 ml/vial |
| | 170904 | 20 ml/vial |
| | 171002 | 20 ml/vial |
| | 171202 | 20 ml/vial |
| | 171203 | 20 ml/vial |
| | 171204 | 20 ml/vial |
| | 171205 | 20 ml/vial |
| | 171207 | 20 ml/vial |
| | 180101 | 20 ml/vial |
| | 180301 | 20 ml/vial |
| | 180304 | 20 ml/vial |
| | 151011 | 10 ml/vial |
| | 151106 | 10 ml/vial |
| | 151107 | 10 ml/vial |
| | 151108 | 10 ml/vial |
| | 151109 | 10 ml/vial |
| | 161201 | 10 ml/vial |
| | 161206 | 10 ml/vial |
| | 170207 | 10 ml/vial |
| | 170803 | 10 ml/vial |
| | 170901 | 10 ml/vial |
| | 171007 | 10 ml/vial |
| | 171101 | 10 ml/vial |
| | 171104 | 10 ml/vial |
| | 171107 | 10 ml/vial |
| | 171109 | 10 ml/vial |

Preparation of reference solution An appropriate amount of icariin reference standards were accurately weighed and prepared into a solution of 100 μg/ml, which was shaken well to obtain the reference solution.

Preparation of test solution 2 ml each of 15 lots of Shengbai oral solution (20 ml/vial) and 2 ml each of 15 lots of Shengbai oral solution (10 ml/vial) were accurately measured respectively, transferred into 10 ml flasks, diluted with water to scale, shaken well, filtered to get the subsequent filtrates as the test solutions.

[fingerprint] Detect according to HPLC method (CP 2015, Volume IV, General Chapter 0512).

Using octadecylsilane chemically bonded silica as filler (column length 25 cm, inner diameter 4.6 mm, particle size 5 μm); acetonitrile as mobile phase A and 0.1% formic acid as mobile phase B, conducting gradient elution based on the following table; detection wavelength 270 nm; column temperature 30° C.; flow rate 1.0 ml/min; theoretical plate number not less than 10000 calculated based on icariin peak.

Table of gradient elution, fingerprint detection of Shengbai oral solution

| Time(min) | Mobile phase A(%) | Mobile phase B(%) |
|---|---|---|
| 0~10 | 2→6 | 98→94 |
| 10~31 | 6→23 | 94→77 |
| 31~40 | 23→26 | 77→74 |
| 40~56 | 26→53 | 74→47 |
| 56~60 | 53→80 | 47→20 |
| 60~70 | 80→80 | 20→20 |

Test method 10 μl each of the reference solution and test solution were accurately taken, then injected into the liquid chromatograph to record the chromatogram for 70 minutes. Fingerprint similarity evaluation software was adopted to calculate the results and generate the comparison fingerprints. Results showed that the similarity of 15 lots of Shengbai oral solution (20 ml/vial) was 0.991~0.999, and that of 15 lots of Shengbai oral solution (10 ml/vial) was 0.987~0.999, indicating a good reproducibility and relatively stable process of the oral solution.

Common peak marking: Integration time of chromatogram: 0~70 min; Integration parameters: Peak width of 30, minimum peak area of 1, minimum peak height of 1. Within the fingerprints of 15 lots each of Shengbai oral solution (20 ml/vial) and Shengbai oral solution (10 ml/vial) samples, the chromatographic peaks with good peak patterns, high resolutions and peak areas accounting for 0.8% of the total peak area were selected for marking.

The similarity of 15 lots of Shengbai oral solution (20 ml/vial) was 0.991~0.999, and that of 15 lots of Shengbai oral solution (10 ml/vial) was 0.987~0.999, with the average similarity of 0.993, comprehensively considering other factors, the similarity of fingerprint of Shengbai oral solution was provisionally set at the level of not being less than 0.85. The 14 common peaks marked include leucine, guanosine, psoralenoside, isopsoralenoside, calycosin-7-glucoside, liquiritin, icariin A, 1,3-dihydroxy-2-hydroxymethylanthraquinone, epimedin A, epimedin B, epimedin C, icariin, 1,3,6-trihydroxy-2-methylanthraquinone, glycyrrhizic acid.

TABLE 14

Retention time and peak areas of common peaks, based on fingerprints of 15 lots of Shengbai oral solution (10 ml/vial)

| | 151011 | | 151108 | | 161206 | | 170901 | |
|---|---|---|---|---|---|---|---|---|
| Peak | Retention time | Peak area | Retention time | Peak area | Retention time | Peak area | Retention time | Peak area |
| 1 | 5.617 | 1173709 | 5.623 | 1289161 | 5.636 | 1052686 | 5.639 | 1000671 |
| 2 | 7.615 | 277414 | 7.582 | 479362 | 7.591 | 437915 | 7.587 | 532143 |

TABLE 14-continued

Retention time and peak areas of common peaks, based on fingerprints of 15 lots of Shengbai oral solution (10 ml/vial)

| | | | | | | | | |
|---|---|---|---|---|---|---|---|---|
| 3 | 26.822 | 576309 | 26.738 | 964385 | 26.788 | 1034371 | 26.846 | 979233 |
| 4 | 27.628 | 451572 | 27.538 | 881777 | 27.588 | 948575 | 27.629 | 723561 |
| 5 | 29.737 | 335559 | 29.631 | 499380 | 29.682 | 450756 | 29.685 | 666502 |
| 6 | 30.835 | 948222 | 30.7 | 1207170 | 30.762 | 1146035 | 30.763 | 1459540 |
| 7 | 36.768 | 504708 | 36.555 | 518298 | 36.457 | 484178 | 36.488 | 643250 |
| 8 | 41.518 | 1559279 | 41.214 | 1666274 | 41.024 | 1096298 | 41.129 | 1306327 |
| 9 | 44.215 | 703217 | 43.943 | 605134 | 43.661 | 734651 | 43.806 | 725901 |
| 10 | 44.958 | 1149848 | 44.754 | 899506 | 44.545 | 1375417 | 44.659 | 1388946 |
| 11 | 45.558 | 2906515 | 45.398 | 2963397 | 45.224 | 2900992 | 45.326 | 3046505 |
| 12 | 46.436 | 5055032 | 46.301 | 5065248 | 46.161 | 5459449 | 46.251 | 6015263 |
| 13 | 49.022 | 830111 | 48.919 | 903647 | 48.832 | 1121002 | 48.905 | 1221697 |
| 14 | 52.912 | 417637 | 52.819 | 714707 | 52.753 | 501981 | 52.804 | 588391 |

| | 171101 | | 151107 | | 151109 | | 170207 | |
|---|---|---|---|---|---|---|---|---|
| Peak | Retention time | Peak area | Retention time | Peak area | Retention time | Peak area | Retention time | Peak area |
| 1 | 5.671 | 907823 | 5.607 | 1308365 | 5.665 | 1296292 | 5.647 | 905375 |
| 2 | 7.689 | 567962 | 7.593 | 440752 | 7.662 | 424929 | 7.577 | 421531 |
| 3 | 26.943 | 1588178 | 26.832 | 1616508 | 26.719 | 1457461 | 26.767 | 778943 |
| 4 | 27.734 | 1356727 | 27.693 | 1654218 | 27.514 | 1306189 | 27.57 | 720842 |
| 5 | 29.819 | 642065 | 29.799 | 421802 | 29.609 | 438030 | 29.656 | 462671 |
| 6 | 30.895 | 1489566 | 30.875 | 1182228 | 30.699 | 1252428 | 30.737 | 1291460 |
| 7 | 36.681 | 651198 | 36.791 | 501388 | 36.488 | 533024 | 36.415 | 538764 |
| 8 | 41.344 | 1235225 | 41.52 | 1650979 | 41.141 | 1832174 | 40.975 | 1166995 |
| 9 | 44.012 | 685320 | 44.203 | 578820 | 43.82 | 634395 | 43.6 | 747007 |
| 10 | 44.801 | 1475572 | 44.952 | 863136 | 44.665 | 892082 | 44.558 | 1412713 |
| 11 | 45.431 | 2873841 | 45.558 | 2835329 | 45.321 | 3006971 | 45.267 | 2993764 |
| 12 | 46.33 | 5701311 | 46.442 | 4798808 | 46.237 | 5289941 | 46.206 | 5705031 |
| 13 | 48.953 | 1329727 | 49.041 | 918033 | 48.871 | 847657 | 48.892 | 1191975 |
| 14 | 52.879 | 503948 | 52.932 | 363056 | 52.758 | 660790 | 52.815 | 489957 |

| | 171007 | | 171107 | | 151006 | | 161201 | |
|---|---|---|---|---|---|---|---|---|
| Peak | Retention time | Peak area | Retention time | Peak area | Retention time | Peak area | Retention time | Peak area |
| 1 | 5.66 | 1037215 | 5.745 | 964074 | 5.601 | 812441 | 5.639 | 1040209 |
| 2 | 7.601 | 616167 | 7.738 | 630946 | 7.564 | 225925 | 7.6 | 451479 |
| 3 | 26.801 | 1433682 | 26.85 | 1407628 | 26.737 | 964907 | 26.792 | 738859 |
| 4 | 27.584 | 1236266 | 27.649 | 1236113 | 27.544 | 784411 | 27.592 | 686776 |
| 5 | 29.64 | 670602 | 29.765 | 410846 | 29.671 | 268446 | 29.687 | 355082 |
| 6 | 30.717 | 1509022 | 30.855 | 1484963 | 30.712 | 846269 | 30.765 | 1088238 |
| 7 | 36.441 | 622704 | 36.679 | 652625 | 36.693 | 483579 | 36.486 | 445717 |
| 8 | 41.081 | 1296801 | 41.344 | 1136879 | 41.383 | 1771575 | 41.079 | 1056623 |
| 9 | 43.755 | 720849 | 43.993 | 814135 | 44.144 | 691867 | 43.742 | 683533 |
| 10 | 44.614 | 1497869 | 44.788 | 1401556 | 44.91 | 1228442 | 44.602 | 1306433 |
| 11 | 45.288 | 3076908 | 45.416 | 3337063 | 45.525 | 2758636 | 45.267 | 2675443 |
| 12 | 46.215 | 6078041 | 46.315 | 6521470 | 46.413 | 5204994 | 46.194 | 5142659 |
| 13 | 48.884 | 1401572 | 48.912 | 1232470 | 49.005 | 994617 | 48.858 | 994302 |
| 14 | 52.799 | 600678 | 52.786 | 581555 | 52.913 | 444311 | 52.773 | 478650 |

| | 170803 | | 171104 | | 171109 | |
|---|---|---|---|---|---|---|
| Peak | Retention time | Peak area | Retention time | Peak area | Retention time | Peak area |
| 1 | 5.69 | 1135512 | 5.675 | 1048592 | 5.61 | 983199 |
| 2 | 7.624 | 613218 | 7.625 | 676693 | 7.531 | 637143 |
| 3 | 26.801 | 926724 | 26.805 | 1515319 | 26.639 | 1812181 |
| 4 | 27.588 | 791699 | 27.602 | 1328871 | 27.427 | 1717791 |
| 5 | 29.651 | 457248 | 29.682 | 651217 | 29.515 | 711661 |
| 6 | 30.732 | 1487743 | 30.758 | 1534456 | 30.559 | 1608016 |
| 7 | 36.506 | 630043 | 36.466 | 698890 | 36.437 | 711115 |
| 8 | 41.195 | 1301599 | 41.069 | 1246680 | 41.039 | 1307561 |
| 9 | 43.908 | 706629 | 43.726 | 754696 | 43.813 | 764396 |
| 10 | 44.738 | 1316850 | 44.596 | 1493861 | 44.665 | 1509274 |
| 11 | 45.39 | 2892935 | 45.275 | 3139483 | 45.328 | 3388547 |
| 12 | 46.302 | 5654281 | 46.213 | 6129244 | 46.242 | 6785488 |
| 13 | 48.934 | 1272587 | 48.904 | 1426376 | 48.854 | 1509678 |
| 14 | 52.832 | 622820 | 52.856 | 560503 | 52.788 | 618662 |

TABLE 15

Retention time and peak areas of common peaks, based on fingerprints of 15 lots of Shengbai oral solution (20 ml/vial)

| | 180304 | | 160304 | | 170904 | | 171202 | |
|---|---|---|---|---|---|---|---|---|
| Peak | Retention time | Peak area | Retention time | Peak area | Retention time | Peak area | Retention time | Peak area |
| 1 | 5.697 | 927649 | 5.681 | 1172799 | 5.653 | 1234410 | 5.583 | 1088981 |
| 2 | 7.717 | 630280 | 7.678 | 406901 | 7.63 | 402705 | 7.57 | 735710 |
| 3 | 26.871 | 1567341 | 26.899 | 774976 | 26.936 | 1661819 | 26.754 | 2156173 |
| 4 | 27.663 | 1288934 | 27.702 | 703186 | 27.731 | 1399018 | 27.565 | 1971411 |
| 5 | 29.745 | 626850 | 29.777 | 511912 | 29.825 | 593112 | 29.682 | 826714 |
| 6 | 30.83 | 1391701 | 30.855 | 1122728 | 30.942 | 1574717 | 30.765 | 2038606 |
| 7 | 36.644 | 786220 | 36.609 | 552494 | 36.719 | 724673 | 36.537 | 1001102 |
| 8 | 41.305 | 1306480 | 41.262 | 1640289 | 41.317 | 1533342 | 41.157 | 1612793 |
| 9 | 43.982 | 916571 | 43.95 | 831715 | 44.091 | 827114 | 43.817 | 1179174 |
| 10 | 44.788 | 1622408 | 44.76 | 1384529 | 44.876 | 1545960 | 44.669 | 1989989 |
| 11 | 45.424 | 3607264 | 45.392 | 3096666 | 45.491 | 3216434 | 45.328 | 4392527 |
| 12 | 46.323 | 7409928 | 46.289 | 5963992 | 46.371 | 6553326 | 46.242 | 8689524 |
| 13 | 48.919 | 1893075 | 48.884 | 988301 | 48.945 | 1484064 | 48.849 | 1941169 |
| 14 | 52.801 | 711753 | 52.762 | 488081 | 52.815 | 667467 | 52.743 | 756871 |

| | 180101 | | 160302 | | 170603 | | 171002 | |
|---|---|---|---|---|---|---|---|---|
| Peak | Retention time | Peak area | Retention time | Peak area | Retention time | Peak area | Retention time | Peak area |
| 1 | 5.633 | 947272 | 5.68 | 1207202 | 5.665 | 984746 | 5.638 | 1246937 |
| 2 | 7.592 | 637873 | 7.676 | 343332 | 7.65 | 477011 | 7.639 | 427183 |
| 3 | 26.781 | 1762466 | 26.884 | 1285699 | 26.825 | 872813 | 26.895 | 1633036 |
| 4 | 27.592 | 1557906 | 27.684 | 1222181 | 27.628 | 774143 | 27.7 | 1456854 |
| 5 | 29.708 | 689217 | 29.745 | 413077 | 29.728 | 491428 | 29.793 | 555752 |
| 6 | 30.78 | 1663270 | 30.821 | 1106340 | 30.805 | 1257075 | 30.867 | 1502960 |
| 7 | 36.573 | 802278 | 36.549 | 516256 | 36.587 | 661428 | 36.632 | 698487 |
| 8 | 41.196 | 1439704 | 41.136 | 1879976 | 41.225 | 1209798 | 41.29 | 1409040 |
| 9 | 43.859 | 904803 | 43.785 | 862927 | 43.908 | 818495 | 43.969 | 901338 |
| 10 | 44.695 | 1558201 | 44.641 | 1286676 | 44.733 | 1456617 | 44.777 | 1445086 |
| 11 | 45.34 | 3602280 | 45.3 | 3090143 | 45.371 | 3206804 | 45.41 | 3182719 |
| 12 | 46.25 | 7204596 | 46.215 | 5447871 | 46.273 | 6271367 | 46.302 | 6289819 |
| 13 | 48.86 | 1568431 | 48.84 | 1059293 | 48.894 | 1367738 | 48.894 | 1449251 |
| 14 | 52.763 | 647568 | 52.732 | 612373 | 52.773 | 521825 | 52.795 | 667025 |

| | 171204 | | 180301 | | 160303 | | 170902 | |
|---|---|---|---|---|---|---|---|---|
| Peak | Retention time | Peak area | Retention time | Peak area | Retention time | Peak area | Retention time | Peak area |
| 1 | 5.645 | 971429 | 5.594 | 949550 | 5.665 | 1196995 | 5.648 | 1120125 |
| 2 | 7.609 | 666503 | 7.552 | 634128 | 7.65 | 297249 | 7.859 | 427557 |
| 3 | 26.871 | 1739996 | 26.77 | 1740377 | 26.825 | 835312 | 26.792 | 1348276 |
| 4 | 27.677 | 1568980 | 27.58 | 1618192 | 27.628 | 583983 | 27.592 | 988315 |
| 5 | 29.766 | 726264 | 29.726 | 640246 | 29.728 | 504444 | 29.682 | 63799 |
| 6 | 30.848 | 1684376 | 30.805 | 1607557 | 30.805 | 1228157 | 30.758 | 1607071 |
| 7 | 36.568 | 696776 | 36.65 | 727171 | 36.587 | 508024 | 36.557 | 574568 |
| 8 | 41.18 | 1465211 | 41.325 | 1326577 | 41.225 | 1456713 | 41.204 | 1409587 |
| 9 | 43.845 | 876450 | 44.023 | 854211 | 43.908 | 70613 | 43.889 | 812621 |
| 10 | 44.685 | 1657856 | 44.822 | 1533682 | 44.733 | 1064258 | 44.72 | 1577652 |
| 11 | 45.334 | 3527758 | 45.451 | 3560299 | 45.371 | 2957408 | 45.372 | 3193504 |
| 12 | 46.243 | 7056511 | 46.343 | 7025802 | 46.273 | 5514386 | 46.284 | 6195326 |
| 13 | 48.844 | 1598122 | 48.918 | 1558022 | 48.894 | 1029473 | 48.919 | 1427036 |
| 14 | 52.714 | 628620 | 52.797 | 629451 | 52.773 | 581626 | 52.828 | 611.838 |

| | 171203 | | 171205 | | 171207 | |
|---|---|---|---|---|---|---|
| Peak | Retention time | Peak area | Retention time | Peak area | Retention time | Peak area |
| 1 | 5.55 | 1414582 | 5.631 | 983.753 | 5.58 | 1065356 |
| 2 | 7.543 | 82738 | 7.687 | 596.382 | 7.566 | 643063 |
| 3 | 26.654 | 2455499 | 26.937 | 1916.194 | 26.787 | 1880597 |
| 4 | 27.465 | 2068538 | 27.74 | 1668.563 | 27.598 | 164387 |
| 5 | 29.58 | 90696 | 29.857 | 677.514 | 29.676 | 720028 |
| 6 | 30.657 | 2340311 | 30.939 | 1782.836 | 30.748 | 1818672 |
| 7 | 36.413 | 876814 | 36.744 | 667.308 | 36.562 | 697398 |
| 8 | 41.006 | 1719622 | 41.459 | 1345.05 | 41.16 | 1346073 |
| 9 | 43.646 | 1273978 | 44.21 | 795.843 | 43.899 | 906752 |
| 10 | 44.536 | 2093408 | 44.962 | 1650.886 | 44.764 | 1671137 |
| 11 | 45.216 | 4705229 | 45.564 | 3631.176 | 45.416 | 3933584 |
| 12 | 46.148 | 9211836 | 46.437 | 7010.378 | 46.299 | 7642561 |

TABLE 15-continued

Retention time and peak areas of common peaks, based on fingerprints of 15 lots of Shengbai oral solution (20 ml/vial)

| 13 | 48.786 | 205742 | 48.987 | 1573.616 | 48.848 | 1610911 |
| 14 | 52.693 | 782229 | 52.863 | 670.302 | 52.728 | 675571 |

The foregoing descriptions of specific examples and embodiments of the invention are for the purpose of exemplifying and illustration. These descriptions are not intended to limit the invention to the exact form disclosed, and it is clear that many changes and variations can be made according to the above instruction. The purpose of selecting and describing the exemplary examples and embodiments is to explain the specific principles of the invention and practical applications thereof so that the various exemplary embodiments and the various options and variations of the invention can be realized and utilized by technicians in the field. The scope of the invention is subject to what is claimed and its equivalent thereof.

The invention claimed is:

1. A drug for treating leukopenia, which comprises 200-30 parts by weight of Folium Epimedii, 100-160 parts by weight of Fructus Psoraleae, 60-120 parts by weight of Radix Aconiti Lateralis Preparata (Processed), 200-300 parts by weight of Fructus Lycii, 200-300 parts by weight of Radix Astragali, 200-300 parts by weight of Caulis Spatholobi, 200-300 parts by weight of Radix Rubiae, 100-160 parts by weight of Radix Angelicae Sinensis, 200-300 parts by weight of Rhizoma Phragmitis, 100-160 parts by weight of Radix Ophiopogonis, and 100-160 parts by weight of Radix et Rhizoma Glycyrrhizae, wherein said drug comprises chemical substances with weight ratios as follows:Leucine:guanosine:psoralenoside:isopsoralenoside: calycosin-7-glucoside:liquiritin:icariin A:1,3-dihydroxyl-2-hydroxymethylanthraquinone:epimedin A:epimedin B:epimedin C:icariin:1,3,6-trihydroxy-2-methylanthraquinone: glycyrrhizic acid=(0.13-0.27):(0.04-0.11):(0.11-0.34):(0.09-0.34):(0.05-0.11):(0.16-0.26):(0.09-0.12):(0.17-0.35):(0.11-0.16):(0.17-0.26):(0.49-0.59):1.00:(0.16-0.24):(0.08-0.14).

2. The drug for treating leukopenia of claim 1, comprising 240 parts by weight of Folium Epimedii, 120 parts by weight of Fructus Psoraleae, 80 parts by weight of Radix Aconiti Lateralis Preparata (Processed), 240 parts by weight of Fructus Lycii, 240 parts by weight of Radix Astragali, 240 parts by weight of Caulis Spatholobi, 240 parts by weight of Radix Rubiae, 120 parts by weight of Radix Angelicae Sinensis, 240 parts by weight of Rhizoma Phragmitis, 120 parts by weight of Radix Ophiopogonis, and 120 parts by weight of Radix et Rhizoma Glycyrrhizae.

3. The drug for treating leukopenia of claim 1, wherein said drug comprises chemical substances with weight ratios as follows: Leucine:guanosine:psoralenoside:isopsoralenoside:calycosin-7-glucoside:liquiritin:icariin A:1,3-dihydroxyl-2-hydroxymethylanthraquinone:epimedin A:epimedin B:epimedin C:icariin:1,3,6-trihydroxy-2-methylanthraquinone:glycyrrhizic acid=(0.13-0.22):(0.06-0.10):(0.14-0.26):(0.12-0.23):(0.07-0.11):(0.19-0.25):(0.10-0.12):(0.18-0.28):(0.11-0.14):(0.21-0.25):(0.50-0.54): 1.00: (0.19-0.23):(0.09-0.11).

4. The drug for treating leukopenia of claim 1, wherein said chemical substances have the following relative retention time (RRT) according to ultra performance liquid chromatography (UPLC):Leucine 0.120-0.124, guanosine 0.163-0.167, psoralenoside 0.576-0.582, isopsoralenoside 0.593-0.599, calycosin-7-glucoside 0.638-0.644, liquiritin 0.661-0.667, icariin A 0.788-0.792, 1,3-dihydroxyl-2-hydroxymethylanthraquinone 0.887-0.894, epimedin A 0.944-0.952, epimedin B 0.964-0.968, epimedin C 0.980-0.981, icariin 1.000, 1,3,6-trihydroxy-2-methylanthraquinone 1.055-1.058, glycyrrhizic acid 1.138-1.144.

5. A pharmaceutical preparation, comprising the drug of claim 1, further comprising one or more pharmaceutically acceptable carriers, in which the drug accounts for 0.1-99.9% (weight percentage), the rest being pharmaceutically acceptable carriers.

6. The pharmaceutical preparation of claim 5, wherein said pharmaceutical preparation is an oral solution or granule.

7. A method of preparing a drug for treating leukopenia according to claim 1, comprising steps of:

Step (1): Taking 200-30 parts by weight of Folium Epimedii, 100-160 parts by weight of Fructus Psoraleae, 60-120 parts by weight of Radix Aconiti Lateralis Preparata (Processed), 200-300 parts by weight of Fructus Lycii, 200-300 parts by weight of Radix Astragali, 200-300 parts by weight of Caulis Spatholobi, 200-300 parts by weight of Radix Rubiae, 100-160 parts by weight of Radix Angelicae Sinensis, 200-300 parts by weight of Rhizoma Phragmitis, 100-160 parts by weight of Radix Ophiopogonis and 100-160 parts by weight of Radix et Rhizoma Glycyrrhizae, standby;

Step (2): Adding water into the above formulated amount of 10 kinds of prepared slices of Chinese crude drugs (not including Folium Epimedii) and heating to boiling, then adding the formulated amount of Folium Epimedii, continuing heating to boiling, carrying out timing extraction, then filtering to get the filtrate for the first time, adding water to the residues for a second-time extraction, filtering to get the filtrate for the second time, combining the two-time filtrates, concentrating to get the extract I;

Step (3): Slowly adding 85-95% ethanol into the extract I at the ratio of extract I:ethanol=1:1-2, adding while stirring, so that extract I can be evenly dispersed, then adding 85-95% ethanol to alcohol content of 60-80%, adding while stirring, standing, then recovering ethanol, to obtain Shengbai extract.

8. The preparation method of claim 7, wherein said step (2): Adding water into the formulated amount of 10 kinds of prepared slices of Chinese crude drugs (not including Folium Epimedii) and heating at 75-100° C. to boiling, then adding the formulated amount of Folium Epimedii, continuing heating at 75-100° C. to boiling, extracting for 0.5-1.5 h, then filtering to get the filtrate for the first time, adding water to the residues for a second-time extraction, filtering to get the filtrate for the second time, combining the two-time filtrates, concentrating to relative density of 1.24-1.27(25+5° C.) to get the extract I;

Wherein said step (3): Slowly adding 90% ethanol into the extract I at the ratio of extract I:ethanol=1:1-1.2, adding while stirring, so that the extract can be evenly dispersed, then adding 90% ethanol to alcohol content of 70%, adding while stirring, standing for 48-92 h for alcohol precipitation, filtering, recovering ethanol, concentrating to obtain the Shengbai extract.

9. A method of preparing an oral solution for promoting leucocytes, comprising steps of:
Adding purified water and steviosin to the drug prepared according to claim 7, stirring, adjusting pH value to 5.0-6.0, heating to boiling for 30-50 min, refrigerating, taking the supernatant, adjusting pH value to 6.5-7.5, adjusting the volume to required level, filtering, filling, sterilizing.

10. The method of preparing the oral solution of claim 9, wherein said pH regulator is selected from sodium hydroxide solution or sodium bicarbonate solution.

11. A method for treating a person suffering from leukopenia comprising administering a therapeutically effective amount of the composition of claim 1.

12. The drug for treating leukopenia of claim 3, wherein said drug comprises chemical substances with weight ratios as follows: Leucine:guanosine:psoralenoside:isopsoralenoside:calycosin-7-glucoside:liquiritin:icariin A:1,3-dihydroxyl-2-hydroxymethylanthraquinone:epimedinA:epimedinB:epimedin C:icariin:1,3,6-trihydroxy-2-methylanthraquinone: glycyrrhizic acid=(0.14-0.20):(0.06-0.09):(0.19-0.24):(0.17-0.23):(0.09-0.10):(0.23-0.25):(0.10-0.12):(0.20-0.23):(0.12-0.13):(0.22-0.24):(0.51-0.52):1.00:(0.20-0.23):(0.09-0.11).

13. The method of claim 9, further comprising, adding purified water and steviosin to the drug, stirring, adjusting pH value to 5.0-5.5, heating to boiling for 30 min, refrigerating for 48 h, taking the supernatant, adjusting pH value to 7.0-7.3, adjusting the volume to required level, filtering, filling, then sterilizing.

\* \* \* \* \*